(12) United States Patent
Cui et al.

(10) Patent No.: US 9,809,585 B2
(45) Date of Patent: Nov. 7, 2017

(54) FLUORINATED 2-ARYLBENZO HETEROCYCLIC COMPOUND WITH HIGH AFFINITY TO Aβ 946; PLAQUES AND CONTAINING CHIRAL SIDE CHAIN SUBSTITUENT, AND PREPARATION METHOD AND USAGE THEREOF

(71) Applicant: BEIJING ZHIBO BIO-MEDICAL TECHNOLOGY CO.,LTD, Beijing (CN)

(72) Inventors: Mengchao Cui, Beijing (CN); Chunping Lin, Beijing (CN); Boli Liu, Beijing (CN); Yuzhi Guo, Beijing (CN); Zhiyong Zhang, Beijing (CN)

(73) Assignees: BEIJING ZHIBO BIO-MEDICAL TECHNOLOGY CO., LTD, Beijing (CN); Zhiyong Zhang, Beijing (CN)

( * ) Notice: Subject to any disclaimer, the term of this patent is extended or adjusted under 35 U.S.C. 154(b) by 0 days.

(21) Appl. No.: 14/890,922

(22) PCT Filed: Nov. 7, 2014

(86) PCT No.: PCT/CN2014/090536
§ 371 (c)(1),
(2) Date: Nov. 13, 2015

(87) PCT Pub. No.: WO2015/184731
PCT Pub. Date: Dec. 10, 2015

(65) Prior Publication Data
US 2016/0207910 A1    Jul. 21, 2016

(30) Foreign Application Priority Data
Jun. 6, 2014  (CN) .......................... 2014 1 0247965

(51) Int. Cl.
| C07D 417/04 | (2006.01) |
| C07D 413/04 | (2006.01) |
| C07D 263/57 | (2006.01) |
| C07D 277/66 | (2006.01) |
| A61K 51/04 | (2006.01) |
| A61K 49/10 | (2006.01) |

(52) U.S. Cl.
CPC ............ *C07D 417/04* (2013.01); *A61K 49/10* (2013.01); *A61K 51/0453* (2013.01); *A61K 51/0455* (2013.01); *C07D 263/57* (2013.01); *C07D 277/66* (2013.01); *C07D 413/04* (2013.01)

(58) Field of Classification Search
CPC ............................. C07D 417/14; C07D 417/04
USPC ....................................................... 546/270.1
See application file for complete search history.

(56) References Cited

PUBLICATIONS

Cui et al., "Synthesis and, etc.," J. Med. Chem. 2012, 55, 9283-9296.*

* cited by examiner

*Primary Examiner* — Patricia L Morris

(57) ABSTRACT

A fluorinated 2-arylbenzo heterocyclic compound with high affinity to Aβ plaques and containing a chiral side chain substituent, has a general formula (I) as follows:

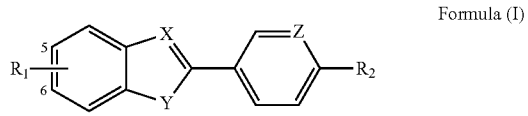

Formula (I)

wherein X is N; Y is S or O; Z is N or CH; $R_1$ is a 5 or 6-substituent and is

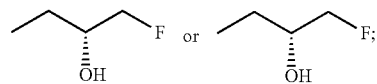

F is $^{19}F$ or $^{18}F$; $R_2$ is $NHCH_3$ or $N(CH_3)_2$. The compound of the present invention has high affinity to Aβ plaques and can be used to make appropriate radioactive nuclide labeling probes for early diagnosis of AD.

1 Claim, 4 Drawing Sheets

FLUORINATED 2-ARYLBENZO HETEROCYCLIC COMPOUND WITH HIGH AFFINITY TO Aβ 946; PLAQUES AND CONTAINING CHIRAL SIDE CHAIN SUBSTITUENT, AND PREPARATION METHOD AND USAGE THEREOF

CROSS REFERENCE OF RELATED APPLICATION

This is a U.S. National Stage under 35 U.S.C 371 of the International Application PCT/CN2014/090536, filed Nov. 7, 2014, which claims priority under 35 U.S.C. 119(a-d) to CN 201410247965.0, filed Jun. 6, 2014.

BACKGROUND OF THE PRESENT INVENTION

Field of Invention

The present invention relates to a fluorinated 2-arylbenzo heterocyclic compound with high affinity to Aβ plaques and containing a chiral side chain substituent, and a preparation method and usage thereof.

Description of Related Arts

Alzheimer's disease (AD) is a progressive fatal neurodegenerative disease with the clinical manifestations including cognitive and memory impairment, and the impairment of the ability for performing activities of daily living, and accompanied with a variety of neuropsychiatric symptoms and behavioral disorders. AD has become a major disease ranking next to cancer, heart disease and stroke and being a serious threat to the health of the elderly. Statistics show that the average incidence rate of AD in people over 65 years is 6.6% and increases with age: 11% in people of 75-80 years old and 22% in people of over 80 years old. At present, China has a rapidly growing aging population. It is estimated that by 2050, the ratio of the elderly of over 60 years old or above will be more than 30%. Therefore, prevention of AD will be an arduous task, and study of early diagnosis of AD is extremely important.

The senile plaques (SPs) deposited outside the nerve cells in the brain and the neuro fibrillary tangles (NFTs) deposited inside the nerve cells in the brain are the two major pathological features of AD. However, its exact pathogenesis is unclear (Hardy J et al., Science, 2002, 297: 353-356). Studies have shown that the deposition of the Aβ plaques in the brain has already been occurring for 10-20 years before AD occurs (Braak, H et al., Acta Neuropathol, 1991, 82: 239-259). Currently, it is difficult to accurately diagnose clinical AD, which is diagnosed mainly by the evaluation of the patient's cognitive dysfunction. AD can be accurately diagnosed only with the SPs and NFTs found in the brain of a patient in an autopsy. Thus, although the causes of AD are unclear yet, early AD can still be diagnosed by an effective non-invasive molecular method in which the Aβ plaques in the brain are used as targets and a molecular probe with high affinity and selectivity to these targets is developed to implement a positron emission tomography (PET) scan (Cai L S et al. Curr Med Chem, 2007, 14: 19-52).

In the past 10 years, there have been a number of positron Aβ molecular probes put into clinical trials, such as the C-11-labeled PIB is the most widely used Aβ imaging agent currently, with which AD can be clearly identified in a patient from normal people. (Klunk W E et al., Annals of Neurology, 2004, 55: 306-319). However, the short half-life (20.4 min) of the C-11 nuclides has limited its application in clinical practice. Therefore, using the F-18-labeled nuclides with a long half-life as an Aβ imaging agent is the current trend of development. For instance, the PIB analogues[18F] GE-067 (Koole M et al., Journal of Nuclear Medicine, 2009, 50:818-22) and the stilbene derivates [18F] AV-45 (Wong D F et al., Journal of Nuclear Medicine, 2010, 51: 913-20) have been approved by FDA, and the commercial development of these compounds has been started.

SUMMARY OF THE PRESENT INVENTION

The present invention is to provide a 2-arylbenzo heterocyclic compound with high affinity to the Aβ plaques in the brain of an AD patient and containing a chiral side chain substituent, and the preparation method and usage thereof.

In the present invention, a fluorinated 2-arylbenzo heterocyclic compound with high affinity to Aβ plaques and containing a chiral side chain substituent is provided. A general formula (I) of the compound is as follows:

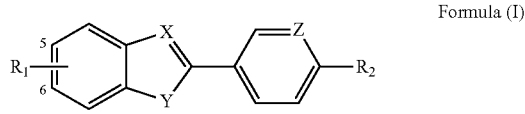

Formula (I)

wherein,

X is N; Y is S or O; Z is N or CH;

R₁ is a 5 or 6-substituent and is

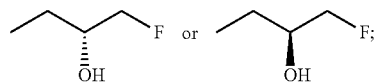

F is $^{19}F$ or $^{18}F$;

R₂ is $NHCH_3$ or $N(CH_3)_2$.

The present invention also provides a preparation method of the compound with the Formula (I). When F in R₁ is $^{19}F$, the preparation method of the compound includes steps of:

(1) dissolving 1 mmol of

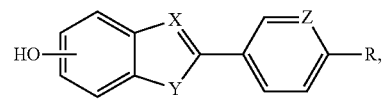

1.5 mmol of

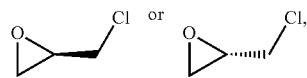 [SMILES: ClC[C@H]1CO1 ; ClC[C@@H]1CO1]

3 mmol of $K_2CO_3$ and a catalytic dose of 18-crown-6 in 30 mL of anhydrous acetone, and stirring a mixture thereof in an oil bath at 80° C. until reflux occurs; after reaction is completed, removing the solvent acetone; wherein after column chromatography separation, a compound with a Formula (II) or a Formula (III) shown below is obtained:

Formula (II)

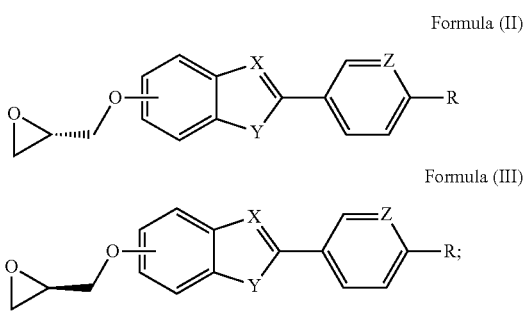

Formula (III)

and (2) dissolving 0.2 mmol of the compound with the Formula (II) or the Formula (III) in 15 mL of toluene; adding 1 mL of a THF solution containing 1M of TBAF to a mixture thereof; stirring the mixture in an oil bath at 80° C. until reflux occurs; after reaction is completed, removing the solvent acetone; wherein after extraction with $CH_2Cl_2$ is completed and the column chromatography separation is completed, a compound with a Formula (IV) or a Formula (V) is obtained:

Formula (IV)

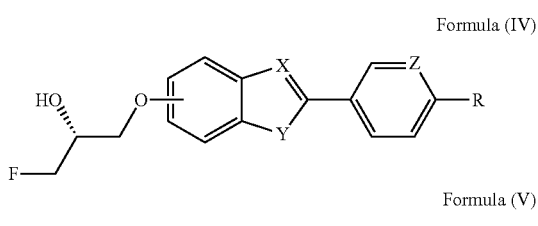

Formula (V)

wherein X is N; Y is S or O; Z is N or CH; R is $NHCH_3$ or $N(CH_3)_2$.

When F in $R_1$ is $^{18}F$ and $R_2$ is $N(CH_3)_2$, a preparation method of the above-mentioned compounds includes steps of:

(1) dissolving 1 mmol of

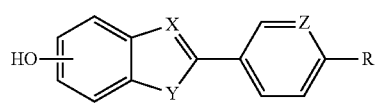

in 30 mL of anhydrous ethanol and adding 0.3 mL of a 200 g/L NaOH solution to a mixture thereof; stirring the mixture in an oil bath at 80° C. until reflux lasts for 1 h; adding 1.5 mmol of

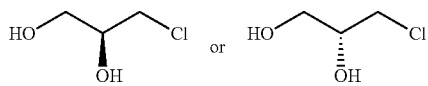 [SMILES: OC[C@H](O)CCl ; OC[C@@H](O)CCl]

to the mixture; after reaction is completed, removing a solvent; wherein after column chromatography separation, a compound with a Formula (VI) or a Formula (VII) shown below is obtained:

Formula (VI)

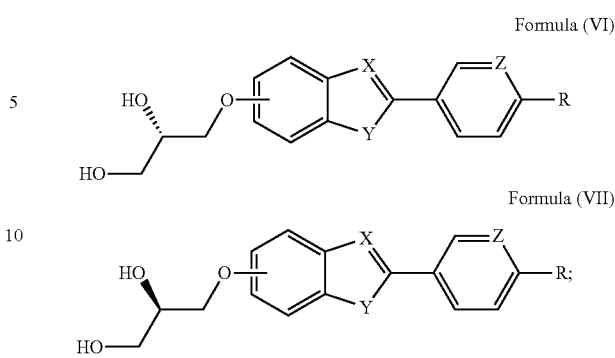

Formula (VII)

(2) when R is $NHCH_3$, dissolving 1 mmol of the compound with the Formula (VI) or the Formula (VII), 8 mmol of imidazole and 8 mmol of tert-butyldimethylsilyl chloride in 30 mL of a $CH_2Cl_2$ solution; stirring a mixture thereof in an oil bath at 40° C. until reflux lasts for 5 h; after reaction is completed, removing $CH_2Cl_2$; wherein after the column chromatography separation, a compound with a Formula (VIII) or a Formula (IX) shown below is obtained:

Formula (VIII)

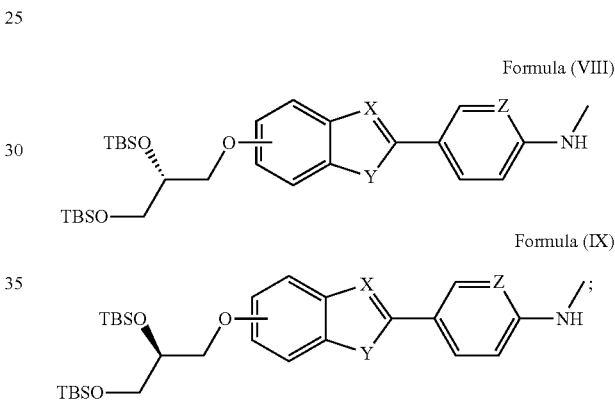

Formula (IX)

(3) dissolving 1 mmol of the compound with the Formula (VIII) or the Formula (IX) in 30 mL of a THF solution and adding an excessive dose of $(Boc)_2O$ to a mixture thereof; stirring the mixture in an oil bath at 80° C. until reflux lasts for a night; after reaction is completed, removing the THF; wherein after the column chromatography separation, a compound with a Formula (X) or a Formula (XI) shown below is obtained:

Formula (X)

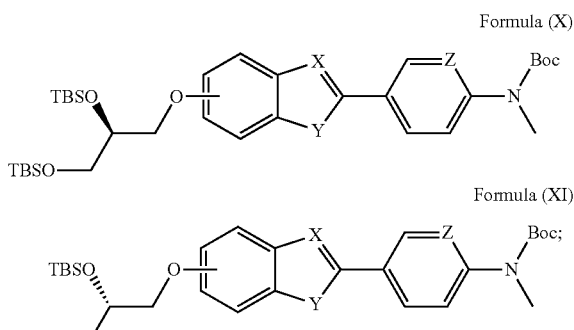

Formula (XI)

(4) dissolving 1 mmol of the compound with the Formula (X) or the Formula (XI) in 30 mL of the THF solution and adding 7 mmol of TBAF to a mixture thereof; stirring the mixture in an oil bath at 30° C. until reflux lasts for one night; after reaction is completed, removing the THF; wherein after the column chromatography separation, a compound with a Formula (XII) or a Formula (XIII) shown below is obtained:

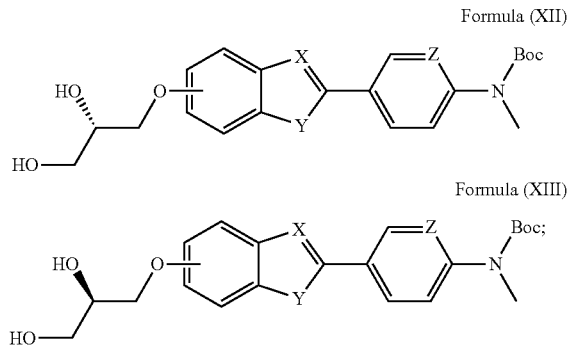

(5) dissolving 1 mmol of the compound (R=NMe₂) with the Formula (VI) or the Formula (VII) and 1 mmol of the compound with the Formula (XII) or the Formula (XIII) in 5 mL of pyridine respectively and adding 1.5 mmol of TsCl to a mixture thereof; stirring the mixture in an ice bath at 0° C. until reactions occur; after the reactions are completed, removing the pyridine; wherein after the column chromatography separation, a compound with a Formula (XIV) or a Formula (XV) shown below is obtained:

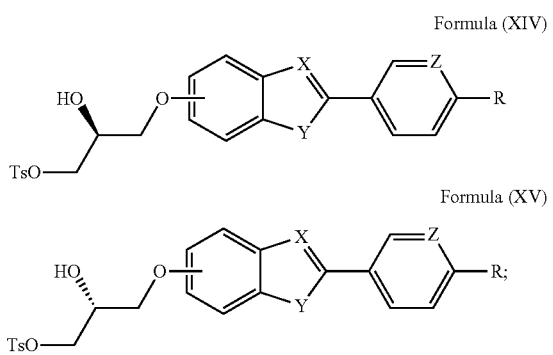

Wherein R is N(CH₃)₂;

(6) dissolving 1 mmol of the compound with the Formula (XIV) or the Formula (XV), 4 mmol of 3,4-dihydro-2H-pyran and 0.2 mmol of PPTS in 30 mL of a CH₂Cl₂ solution respectively; stirring a mixture thereof in an oil bath at 40° C. until reflux lasts for a night; after reaction is completed, removing CH₂Cl₂; wherein after the column chromatography separation, a compound with a Formula (XVI) or a Formula (XVII) shown below is obtained:

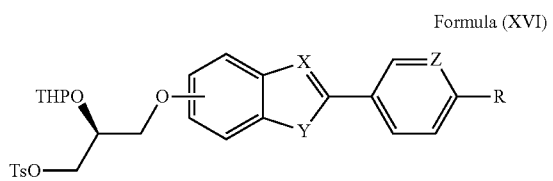

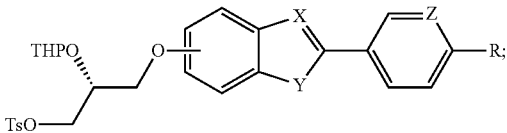

and (7) dissolving 10 mg of the compound with the Formula (XVI) or the Formula (XVII) in 2 mL of acetonitrile; adding a mixture thereof to a reaction tube of dehydrated $^{18}F^-$ of a certain activity and containing $K_{222}/K_2CO_3$; maintaining labeling at 100° C. for 12 min; after the mixture is cooled, adding 0.15 mL of 1M HCl; after swirling is completed, keeping reacting for 5 min; after the mixture is cooled, adding a small amount of water and neutralizing the mixture with NaHCO₃ until the mixture is alkaline; separating the mixture with a C18 reverse phase column and rinsing the mixture with water to remove salts and residual $^{18}F^-$; then rinsing the mixture with the acetonitrile; after the mixture is dried with N₂, separating with HPLC to obtain a compound with a Formula (XVI) or a Formula (XVII) shown below:

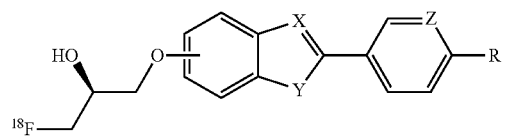

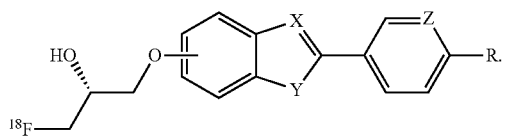

The present invention also provides a method for preparation of an Aβ plaque imaging agent, comprising applying the above mentioned compounds. In the compound with the Formula (I), F is $^{18}F$.

The present invention first provides a 2-arylbenzo heterocyclic compound with a new structure and containing a chiral side chain substituent. In-vitro competitive binding experiments show that the molecules of this category have higher affinity to Aβ₁₋₄₂ plaques. In-vivo biological distribution experiments of normal mice show that with the advantages of high absorption by the primitive brain and fast removal from the brain, some F-18 labeled imaging agents are expected to become new positron Aβ plaque imaging agents for clinical imaging.

BRIEF DESCRIPTION OF THE DRAWINGS

In FIG. 4 and FIG. 5, A is the brain slice of the AD patient, B is the brain slice of the AD transgenic mouse, C is a brain slice of a normal person, and D is a brain slice of a normal mouse.

DETAILED DESCRIPTION OF THE PREFERRED EMBODIMENT

The following embodiments serve to illustrate the present invention but are not intended to limit the scope of the present invention. If not otherwise specified, the technical means used in the embodiments are conventional means known to those skilled in the art, and the materials used are commercially available.

Figure 1:
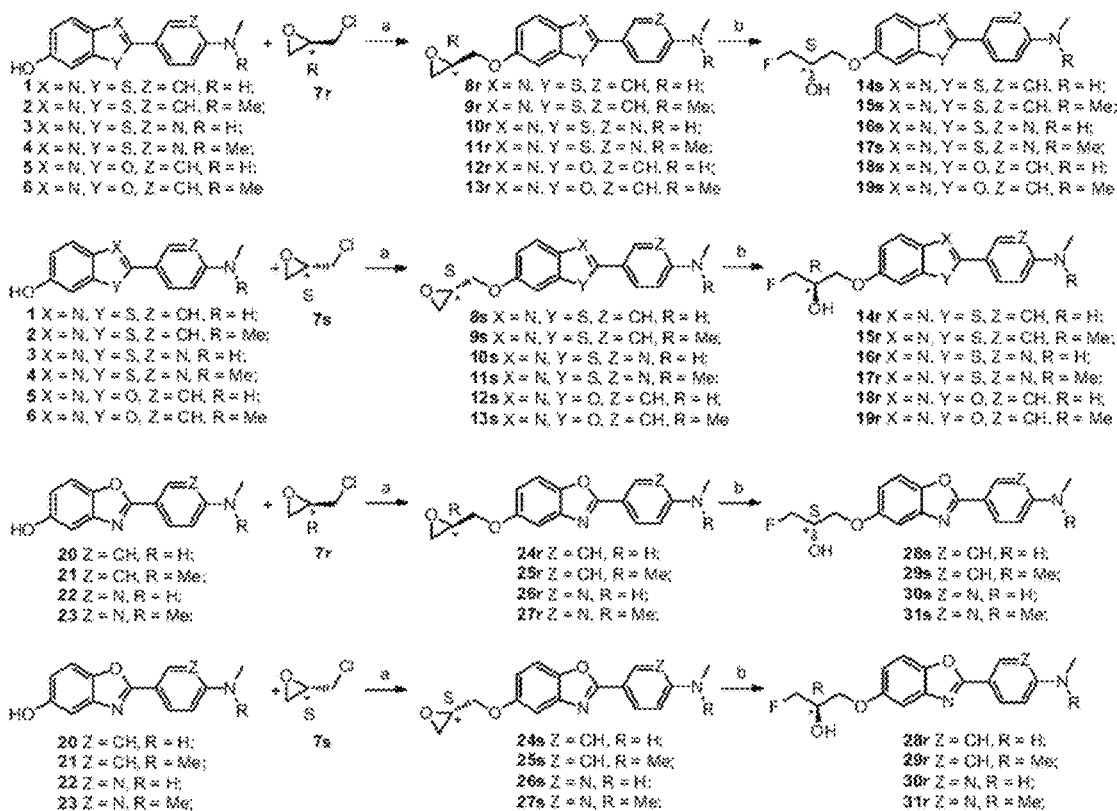
FIG. 1 shows a synthesis process of a 2-arylbenzo heterocyclic compound containing a chiral side chain substituent of the present invention, wherein a represents K₂CO₃, 18-crown-6 and acetone in reflux; b represents TBAF and toluene in the reflux.

Synthesis of a 2-arylbenzo heterocyclic compound containing an optical chiral side chain substituent in provided. Synthesis reaction formulas are shown in FIG. 1. Numbers of compounds used in the following embodiments of the present invention are the same as that used in the formulas shown in FIG. 1.

Figure 2A:
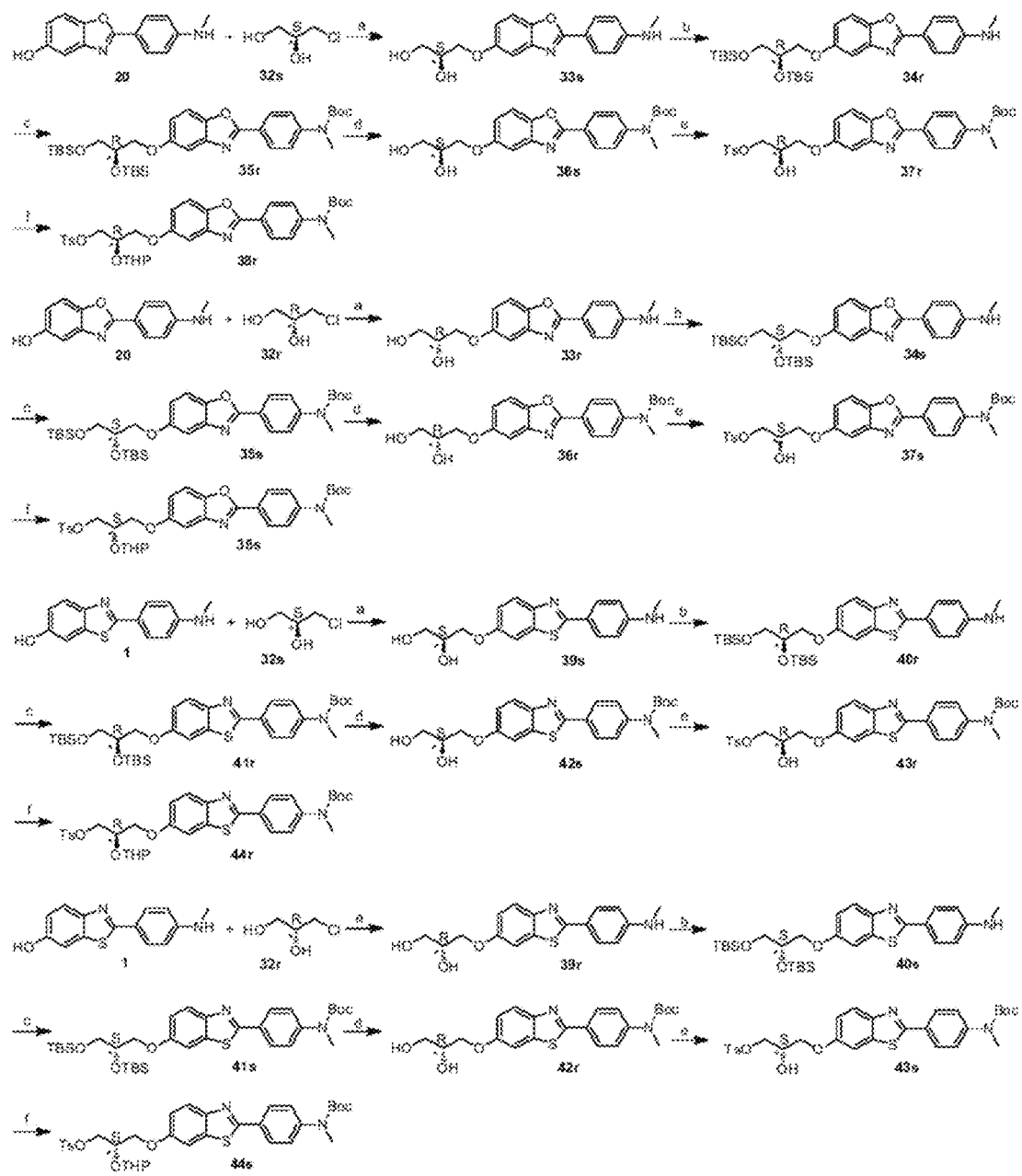
FIG. 2 shows a preparation processes of an F-18 labeled intermediates of the 2-arylbenzo heterocyclic compound containing an optical chiral side chain substituent of the present invention, wherein a represents NaOH, EtOH and H₂O at 90° C.; b represents TBDMSCl, CH₂Cl₂ and imidazole; c represents (Boc)₂O and THF in the reflux; d represents TBAF and THF in the reflux; e represents TsCl and pyridine; f represents PPTS, CH₂Cl₂ and 3,4-dihydro-2H-pyran in the reflux.
Figure 2B:
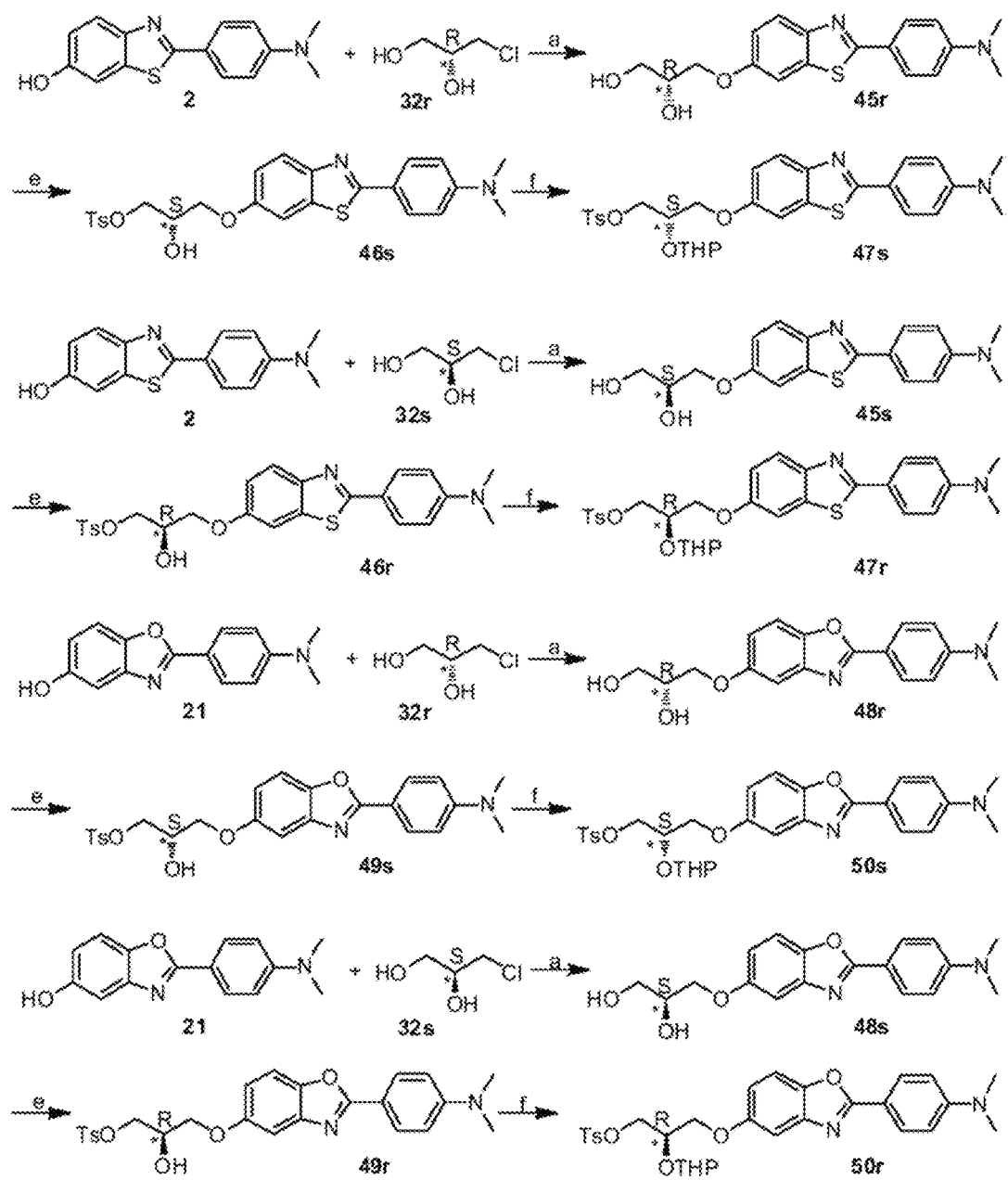
Figure 3:
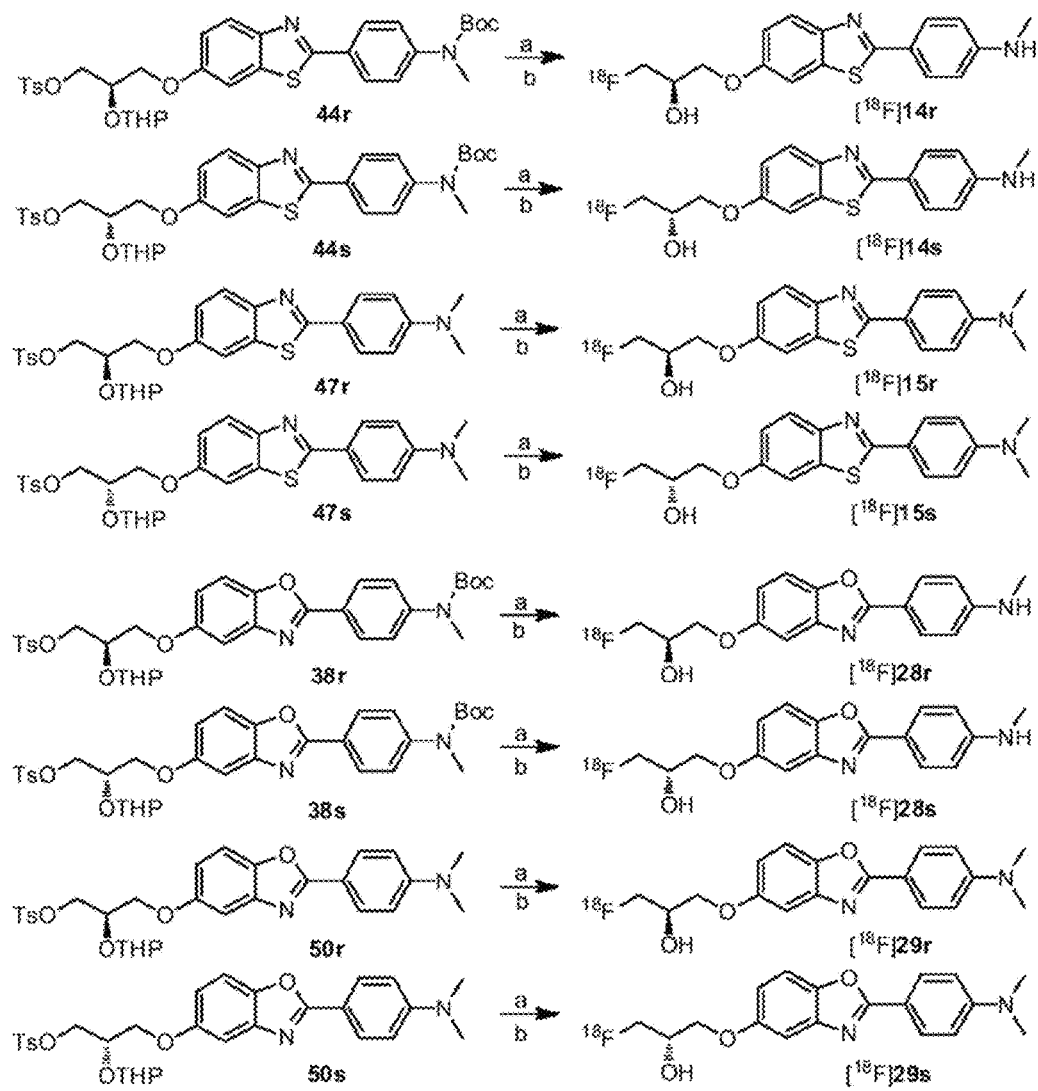
FIG. 3 shows a preparation processes of an F-18 labeled compounds of the present invention, wherein a represents ¹⁸F⁻, K₂CO₃, Kryptofix-2.2.2 and acetonitrile and a reaction temperature is 100° C.; b represents HCl (1M) and the reaction temperature is 100° C.
Figure 4:
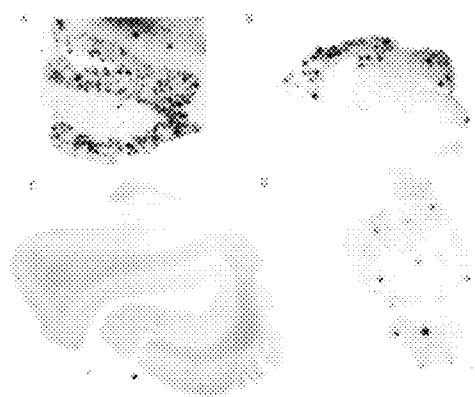
FIG. 4 shows a compound [¹⁸F]29s prepared in Embodiment 84 of the present invention and autoradiography pictures of brain slices of AD patients and AD transgenic mice.
Figure 5:
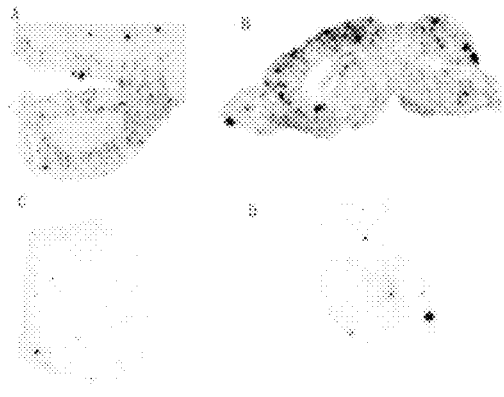
FIG. 5 shows a compound [¹⁸F]29r prepared in Embodiment 83 of the present invention and the autoradiography pictures of the brain slices of AD patients and AD transgenic mice.

Preparation processes of F-18 labeled intermediates of the 2-arylbenzo heterocyclic compound containing the optical chiral side chain substituent are shown in FIG. 2.

Embodiment 1 Synthesis of Intermediate 8r

Dissolve Compound 1 (257.2 mg, 1.0 mmol), K₂CO₃ (435.0 mg, 3.2 mmol) and a catalytic dose of 18-crown-6 in 60 mL of acetone. Add Compound 7r (139.0 mg, 1.5 mmol) to the mixture. Stir the mixture in an oil bath at 80° C. until reflux has occurred for 12 h. After the reaction is completed, remove acetone. After the column chromatography separation, 35.0 mg of Intermediate 8r with the structure shown below and a yield rate of 11.2% can be obtained. ¹H NMR (400 MHz, CDCl₃) δ 7.87 (d, J=8.7 Hz, 2H), 7.86 (d, J=9.0 Hz, 1H), 7.35 (d, J=2.5 Hz, 1H), 7.06 (dd, J=8.9, 2.6 Hz, 1H), 6.64 (d, J=8.7 Hz, 2H), 4.29 (dd, J=11.0, 3.1 Hz, 1H), 4.03 (dd, J=11.0, 5.7 Hz, 1H), 3.42-3.37 (m, 1H), 2.95-2.93 (m, 1H), 2.91 (s, 3H), 2.79 (dd, J=4.9, 2.6 Hz, 1H), MS(ESI): m/z calcd for C₁₇H₁₆N₂O₂S 312.09. found 313.2 (M+H)⁺.

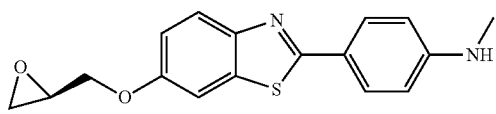

Embodiment 2 Synthesis of Intermediate 8s

Intermediate 8s is prepared by reactions with Compound 1, wherein the ratio of raw materials, the solvents and the reaction conditions are the same as that of Embodiment 1, and the yield rate is 23.0%. ¹HNMR (400 MHz, CDCl₃) δ7.87 (d, J=8.7 Hz, 2H), 7.86 (d, J=8.9 Hz, 1H), 7.34 (d, J=2.5 Hz, 1H), 7.06 (dd, J=8.9, 2.5 Hz, 1H), 6.64 (d, J=8.7 Hz, 2H), 4.29 (dd, J=11.0, 3.1 Hz, 1H), 4.02 (dd, J=11.0, 5.7 Hz, 1H), 3.41-3.36 (m, 1H), 2.94-2.91 (m, 1H), 2.90 (s, 3H), 2.78 (dd, J=4.9, 2.6 Hz, 1H), MS(ESI): m/z calcd for C₁₇H₁₆N₂O₂S 312.09. found 313.1 (M+H)⁺.

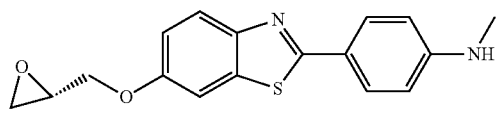 [SMILES: CNc1ccc(-c2nc3ccc(OC[C@@H]4CO4)cc3s2)cc1]

Embodiment 3 Synthesis of Intermediate 9r

Intermediate 9r is prepared by reactions with Compound 2, wherein the ratio of raw materials, the solvents and the reaction conditions are the same as that of Embodiment 1, and the yield rate is 16.4%. ¹H NMR (400 MHz, CDCl₃) δ7.91 (d, J=8.8 Hz, 2H), 7.87 (d, J=8.9 Hz, 1H), 7.34 (d, J=2.5 Hz, 1H), 7.06 (dd, J=8.9, 2.5 Hz, 1H), 6.74 (d, J=8.9 Hz, 2H), 4.29 (dd, J=11.0, 3.1 Hz, 1H), 4.02 (dd, J=11.0, 5.7 Hz, 1H), 3.42-3.37 (m, 1H), 3.05 (s, 6H), 2.93 (t, J=4.5 Hz, 1H), 2.79 (dd, J=4.9, 2.6 Hz, 1H), MS(ESI): m/z calcd for C₁₈H₁₈N₂O₂S 326.11. found 327.2 (M+H)⁺.

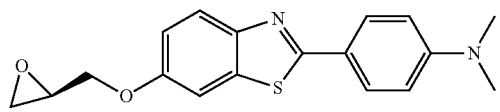 [SMILES: CN(C)c1ccc(-c2nc3ccc(OC[C@H]4CO4)cc3s2)cc1]

Embodiment 4 Synthesis of Intermediate 9s

Intermediate 9s is prepared by reactions with Compound 2, wherein the ratio of raw materials, the solvents and the reaction conditions are the same as that of Embodiment 1, and the yield rate is 34.0%. ¹H NMR (400 MHz, CDCl₃) δ7.91 (d, J=8.9 Hz, 2H), 7.87 (d, J=8.9 Hz, 1H), 7.34 (d, J=2.5 Hz, 1H), 7.06 (dd, J=8.9, 2.5 Hz, 1H), 6.74 (d, J=8.9 Hz, 2H), 4.29 (dd, J=11.0, 3.1 Hz, 1H), 4.02 (dd, J=11.0, 5.7 Hz, 1H), 3.42-3.37 (m, 1H), 3.05 (s, 3H), 2.93 (t, J=4.6 Hz, 1H), 2.78 (dd, J=4.9, 2.6 Hz, 1H), MS(ESI): m/z calcd for C₁₈H₁₈N₂O₂S 326.11. found 327.1 (M+H)⁺.

Embodiment 5 Synthesis of Intermediate 10r

Intermediate 10r is prepared by reactions with Compound 3, wherein the ratio of raw materials, the solvents and the reaction conditions are the same as that of Embodiment 1, and the yield rate is 38.3%. ¹H NMR (400 MHz, CDCl₃) δ8.71 (d, J=2.1 Hz, 1H), 8.12 (dd, J=8.8, 2.3 Hz, 1H), 7.88 (d, J=8.9 Hz, 1H), 7.35 (d, J=2.5 Hz, 1H), 7.09 (dd, J=8.9, 2.5 Hz, 1H), 6.48 (d, J=8.8 Hz, 1H), 5.06 (d, J=4.2 Hz, 1H), 4.31 (dd, J=11.0, 3.0 Hz, 1H), 4.02 (dd, J=11.0, 5.8 Hz, 1H), 3.43-3.39 (m, 1H), 3.01 (d, J=5.1 Hz, 3H), 2.94 (t, J=4.5 Hz, 1H), 2.80 (dd, J=4.9, 2.6 Hz, 1H), MS(ESI): m/z calcd for C₁₆H₁₅N₃O₂S 313.09. found 314.2 (M+H)⁺.

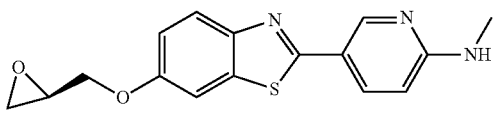 [SMILES: CNc1ccc(-c2nc3ccc(OC[C@H]4CO4)cc3s2)cn1]

Embodiment 6 Synthesis of Intermediate 10s

Intermediate 10s is prepared by reactions with Compound 3, wherein the ratio of raw materials, the solvents and the reaction conditions are the same as that of Embodiment 1, and the yield rate is 31.6%. $^1$H NMR (400 MHz, CDCl$_3$) δ8.71 (d, J=2.1 Hz, 1H), 8.12 (dd, J=8.8, 2.2 Hz, 1H), 7.88 (d, J=8.9 Hz, 1H), 7.36 (d, J=2.4 Hz, 1H), 7.09 (dd, J=8.9, 2.5 Hz, 1H), 6.48 (d, J=8.8 Hz, 1H), 5.05 (d, J=4.0 Hz, 1H), 4.32 (dd, J=11.0, 3.0 Hz, 1H), 4.02 (dd, J=11.0, 5.8 Hz, 1H), 3.43-3.38 (m, 1H), 3.01 (d, J=5.1 Hz, 3H), 2.95 (t, J=4.5 Hz, 1H), 2.80 (dd, J=4.8, 2.6 Hz, 1H), MS(ESI): m/z calcd for C$_{16}$H$_{15}$N$_3$O$_2$S 313.09. found 314.1 (M+H)$^+$.

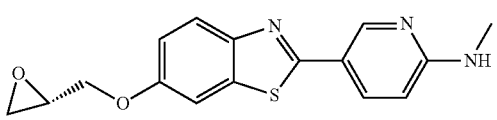 [SMILES: CNc1ccc(-c2nc3ccc(OC[C@@H]4CO4)cc3s2)cn1]

Embodiment 7 Synthesis of Intermediate 11r

Intermediate 11r is prepared by reactions with Compound 4, wherein the ratio of raw materials, the solvents and the reaction conditions are the same as that of Embodiment 1, and the yield rate is 58.8%. $^1$H NMR (400 MHz, CDCl$_3$) δ8.76 (d, J=2.3 Hz, 1H), 8.13 (dd, J=8.9, 2.2 Hz, 1H), 7.87 (d, J=8.9 Hz, 1H), 7.35 (d, J=2.4 Hz, 1H), 7.08 (dd, J=8.9, 2.4 Hz, 1H), 6.59 (d, J=9.0 Hz, 1H), 4.31 (dd, J=11.0, 3.0 Hz, 1H), 4.01 (dd, J=11.0, 5.7 Hz, 1H), 3.43-3.38 (m, 1H), 3.18 (s, 6H), 2.94 (t, J=4.5 Hz, 1H), 2.80 (dd, J=4.8, 2.6 Hz, 1H), MS(ESI): m/z calcd for C$_{17}$H$_{17}$N$_3$O$_2$S 327.10. found 328.2 (M+H)$^+$.

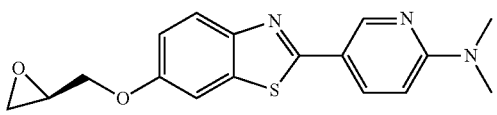 [SMILES: CN(C)c1ccc(-c2nc3ccc(OC[C@H]4CO4)cc3s2)cn1]

Embodiment 8 Synthesis of Intermediate 11s

Intermediate 11s is prepared by reactions with Compound 4, wherein the ratio of raw materials, the solvents and the reaction conditions are the same as that of Embodiment 1, and the yield rate is 70.7%. $^1$H NMR (400 MHz, CDCl$_3$) δ8.76 (d, J=2.3 Hz, 1H), 8.13 (dd, J=9.0, 2.4 Hz, 1H), 7.87 (d, J=8.9 Hz, 1H), 7.35 (d, J=2.5 Hz, 1H), 7.08 (dd, J=8.9, 2.5 Hz, 1H), 6.59 (d, J=9.0 Hz, 1H), 4.31 (dd, J=11.0, 3.0 Hz, 1H), 4.01 (dd, J=11.0, 5.8 Hz, 1H), 3.43-3.38 (m, 1H), 3.18 (s, 6H), 2.95 (t, J=4.5 Hz, 1H), 2.80 (dd, J=4.8, 2.6 Hz, 1H), MS(ESI): m/z calcd for C$_{17}$H$_{17}$N$_3$O$_2$S 327.10. found 328.1 (M+H)$^+$.

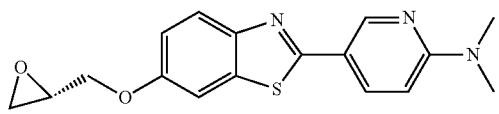 [SMILES: CN(C)c1ccc(-c2nc3ccc(OC[C@@H]4CO4)cc3s2)cn1]

Embodiment 9 Synthesis of Intermediate 12r

Intermediate 12r is prepared by reactions with Compound 5, wherein the ratio of raw materials, the solvents and the reaction conditions are the same as that of Embodiment 1, and the yield rate is 55.3%. $^1$H NMR (400 MHz, CDCl$_3$) δ8.02 (d, J=8.8 Hz, 2H), 7.56 (d, J=8.7 Hz, 1H), 7.10 (d, J=2.3 Hz, 1H), 6.93 (dd, J=8.7, 2.4 Hz, 1H), 6.66 (d, J=8.8 Hz, 2H), 4.29 (dd, J=11.0, 3.1 Hz, 1H), 4.00 (dd, J=11.0, 5.7 Hz, 1H), 3.42-3.38 (m, 1H), 2.99-2.93 (m, 1H), 2.92 (s, 3H), 2.80 (dd, J=4.9, 2.6 Hz, 1H), MS(ESI): m/z calcd for C$_{17}$H$_{16}$N$_2$O$_3$ 296.12. found 297.0 (M+H)$^+$.

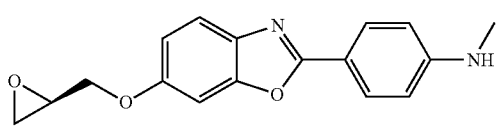 [SMILES: CNc1ccc(-c2nc3ccc(OC[C@H]4CO4)cc3o2)cc1]

Embodiment 10 Synthesis of Intermediate 12s

Intermediate 12s is prepared by reactions with Compound 5, wherein the ratio of raw materials, the solvents and the reaction conditions are the same as that of Embodiment 1, and the yield rate is 51.9%. $^1$H NMR (400 MHz, CDCl$_3$) δ8.03 (d, J=8.8 Hz, 2H), 7.57 (d, J=8.7 Hz, 1H), 7.11 (d, J=2.4 Hz, 1H), 6.93 (dd, J=8.7, 2.4 Hz, 1H), 6.67 (d, J=8.8 Hz, 2H), 4.29 (dd, J=11.0, 3.1 Hz, 1H), 4.01 (dd, J=11.0, 5.7 Hz, 1H), 3.43-3.38 (m, 1H), 2.97-2.93 (m, 1H), 2.92 (s, 3H), 2.80 (dd, J=4.9, 2.6 Hz, 1H), MS(ESI): m/z calcd for C$_{17}$H$_{16}$N$_2$O$_3$ 296.12. found 296.9 (M+H)$^+$.

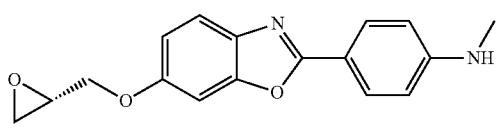 [SMILES: CNc1ccc(-c2nc3ccc(OC[C@@H]4CO4)cc3o2)cc1]

Embodiment 11 Synthesis of Intermediate 13r

Intermediate 13r is prepared by reactions with Compound 6, wherein the ratio of raw materials, the solvents and the reaction conditions are the same as that of Embodiment 1, and the yield rate is 43.5%. $^1$H NMR (400 MHz, CDCl$_3$) δ8.06 (d, J=9.0 Hz, 2H), 7.57 (d, J=8.7 Hz, 1H), 7.11 (d, J=2.3 Hz, 1H), 6.93 (dd, J=8.7, 2.4 Hz, 1H), 6.77 (d, J=9.0 Hz, 2H), 4.29 (dd, J=11.0, 3.1 Hz, 1H), 4.01 (dd, J=11.0, 5.7 Hz, 1H), 3.43-3.38 (m, 1H), 3.07 (s, 6H), 2.98-2.91 (m, 1H), 2.80 (dd, J=4.9, 2.6 Hz, 1H), MS(ESI): m/z calcd for C$_{18}$H$_{18}$N$_2$O$_3$ 310.13. found 310.8 (M+H)$^+$.

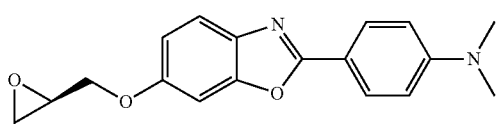 [SMILES: CN(C)c1ccc(-c2nc3ccc(OC[C@H]4CO4)cc3o2)cc1]

Embodiment 12 Synthesis of Intermediate 13s

Intermediate 13s is prepared by reactions with Compound 6, wherein the ratio of raw materials, the solvents and the reaction conditions are the same as that of Embodiment 1, and the yield rate is 28.1%. $^1$H NMR (400 MHz, CDCl$_3$) δ8.06 (d, J=8.7 Hz, 2H), 7.57 (d, J=8.6 Hz, 1H), 7.11 (d, J=1.7 Hz, 1H), 6.93 (dd, J=8.6, 1.8 Hz, 1H), 6.77 (d, J=8.7 Hz, 2H), 4.29 (dd, J=10.9, 2.7 Hz, 1H), 4.01 (dd, J=10.9, 5.7 Hz, 1H), 3.43-3.38 (m, 1H), 3.07 (s, 6H), 2.95 (t, J=4.4 Hz, 1H), 2.88-2.73 (m, 1H), MS(ESI): m/z calcd for C$_{18}$H$_{18}$N$_2$O$_3$ 310.13. found 310.8 (M+H)$^+$.

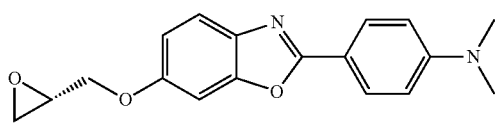 [SMILES: CN(C)c1ccc(-c2nc3ccc(OC[C@@H]4CO4)cc3o2)cc1]

Embodiment 13 Synthesis of Target Compound 14s

Dissolve Intermediate 8r (54.1 mg, 0.17 mmol) in 15 mL of toluene. Add 1 mL of a THF solution (1 mL, 1.0 mmol) containing TBAF to the mixture. Stir the mixture in an oil bath at 80° C. until reflux has occurred for 12 h. After the reaction is completed, remove toluene. Separate the remainder by the column chromatography to obtain 8.4 mg of Target Compound 14s with the structure shown below and a yield rate of 14.9%. $^1$H NMR (400 MHz, DMSO-d$_6$) δ7.77 (d, J=9.0 Hz, 1H), 7.74 (d, J=8.7 Hz, 2H), 7.62 (d, J=2.4 Hz, 1H), 7.05 (dd, J=8.9, 2.4 Hz, 1H), 6.62 (d, J=8.7 Hz, 2H), 5.47 (d, J=4.8 Hz, 1H), 4.59-4.50 (m, 1H), 4.47-4.39 (m, 1H), 4.09-3.98 (m, 3H), 2.73 (d, J=4.8 Hz, 3H), HRMS(EI): m/z calcd for C$_{17}$H$_{18}$N$_2$O$_2$FS 333.1073. found 333.1072 (M+H)$^+$.

Embodiment 14 Synthesis of Target Compound 14r

Target Compound 14r is prepared by reactions with Compound 8s, wherein the ratio of raw materials, the solvents and the reaction conditions are the same as that of Embodiment 13, and the yield rate is 7.4%. $^1$H NMR (400 MHz, DMSO-d$_6$) δ7.77 (d, J=9.0 Hz, 1H), 7.74 (d, J=8.8 Hz, 2H), 7.62 (d, J=2.4 Hz, 1H), 7.05 (dd, J=8.9, 2.5 Hz, 1H), 6.62 (d, J=8.7 Hz, 2H), 5.47 (d, J=5.1 Hz, 1H), 4.60-4.50 (m, 1H), 4.47-4.39 (m, 1H), 4.09-4.01 (m, 3H), 2.73 (d, J=4.9 Hz, 3H), HRMS(EI): m/z calcd for C$_{17}$H$_{18}$N$_2$O$_2$FS 333.1073. found 333.1079 (M+H)$^+$.

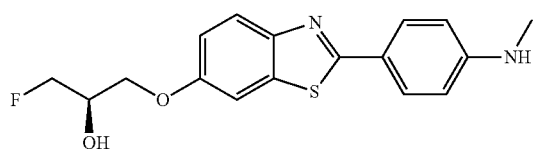 [SMILES: CNc1ccc(-c2nc3ccc(OC[C@@H](O)CF)cc3s2)cc1]

Embodiment 15 Synthesis of Target Compound 15s

Target Compound 15s is prepared by reactions with Intermediate 9r, wherein the ratio of raw materials, the solvents and the reaction conditions are the same as that of Embodiment 13, and the yield rate is 5.8%. $^1$H NMR (400 MHz, CDCl$_3$) δ7.91 (d, J=8.8 Hz, 2H), 7.88 (d, J=9.0 Hz, 1H), 7.33 (d, J=2.4 Hz, 1H), 7.04 (dd, J=8.9, 2.5 Hz, 1H), 6.74 (d, J=8.8 Hz, 2H), 4.72-4.64 (m, 1H), 4.60-4.52 (m, 1H), 4.35-4.24 (m, 1H), 4.17-4.10 (m, 2H), 3.05 (s, 6H), HRMS(EI): m/z calcd for C$_{18}$H$_{20}$N$_2$O$_2$FS 347.1230. found 347.1234 (M+H)$^+$.

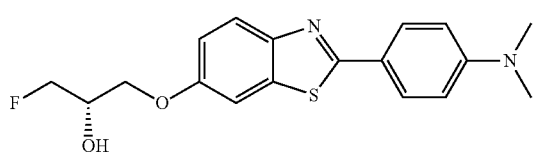

Embodiment 16 Synthesis of Target Compound 15r

Target Compound 15r is prepared by reactions with Intermediate 9s, wherein the ratio of raw materials, the solvents and the reaction conditions are the same as that of Embodiment 13, and the yield rate is 14.8%. $^1$H NMR (400 MHz, CDCl$_3$) δ7.91 (d, J=8.8 Hz, 2H), 7.88 (d, J=8.9 Hz, 1H), 7.33 (d, J=2.4 Hz, 1H), 7.04 (dd, J=8.9, 2.5 Hz, 1H), 6.74 (d, J=8.9 Hz, 2H), 4.72-4.64 (m, 1H), 4.61-4.52 (m, 1H), 4.35-4.24 (m, 1H), 4.15-4.13 (m, 2H), 3.05 (s, 6H), HRMS(EI): m/z calcd for C$_{18}$H$_{20}$N$_2$O$_2$FS 347.1230. found 347.1223 (M+H)$^+$.

Embodiment 17 Synthesis of Target Compound 16s

Target Compound 16s prepared by reactions with Intermediate 10r, wherein the ratio of raw materials, the solvents and the reaction conditions are the same as that of Embodiment 13, and the yield rate is 21.0%. $^1$H NMR (400 MHz, CDCl$_3$) δ8.71 (d, J=1.8 Hz, 1H), 8.12 (dd, J=8.8, 2.2 Hz, 1H), 7.88 (d, J=8.9 Hz, 1H), 7.35 (d, J=2.4 Hz, 1H), 7.07 (dd, J=8.9, 2.5 Hz, 1H), 6.48 (d, J=8.8 Hz, 1H), 5.04 (s, 1H), 4.73-4.65 (m, 1H), 4.61-4.53 (m, 1H), 4.36-4.25 (m, 1H), 4.17-4.15 (m, 2H), 3.01 (d, J=5.1 Hz, 3H), HRMS(EI): m/z calcd for C$_{16}$H$_{17}$N$_3$O$_2$FS 334.1026. found 334.1033 (M+H)$^+$.

Embodiment 18 Synthesis of Target Compound 16r

Target Compound 16r is prepared by reactions with Intermediate 10s, wherein the ratio of raw materials, the solvents and the reaction conditions are the same as that of Embodiment 13, and the yield rate is 14.1%. $^1$H NMR (400 MHz, CDCl$_3$) δ8.68 (d, J=2.0 Hz, 1H), 8.15 (dd, J=8.8, 2.3 Hz, 1H), 7.88 (d, J=8.9 Hz, 1H), 7.36 (d, J=2.5 Hz, 1H), 7.08 (dd, J=8.9, 2.5 Hz, 1H), 6.51 (d, J=8.8 Hz, 1H), 5.27 (s, 1H), 4.73-4.68 (m, 1H), 4.61-4.54 (m, 1H), 4.34-4.27 (m, 1H), 4.17-4.15 (m, 2H), 3.01 (d, J=5.1 Hz, 3H), HRMS(EI): m/z calcd for C$_{16}$H$_{17}$N$_3$O$_2$FS 334.1026. found 334.1022 (M+H)$^+$.

Embodiment 19 Synthesis of Target Compound 17s

Target Compound 17s is prepared by reactions with Intermediate 11r, wherein the ratio of raw materials, the solvents and the reaction conditions are the same as that of Embodiment 13, and the yield rate is 38.6%. $^1$H NMR (400 MHz, CDCl$_3$) δ8.76 (d, J=2.0 Hz, 1H), 8.14 (d, J=8.8 Hz, 1H), 7.88 (d, J=8.9 Hz, 1H), 7.35 (d, J=2.2 Hz, 1H), 7.06 (dd, J=8.9, 2.2 Hz, 1H), 6.59 (d, J=9.0 Hz, 1H), 4.73-4.65 (m, 1H), 4.64-4.53 (m, 1H), 4.33-4.28 (m, 1H), 4.19-4.11 (m, 2H), 3.19 (s, 6H), HRMS(EI): m/z calcd for C$_{17}$H$_{19}$N$_3$O$_2$FS 348.1182. found 348.1188 (M+H)$^+$.

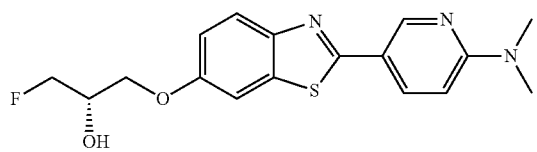 [SMILES: CN(C)c1ccc(-c2nc3ccc(OC[C@H](O)CF)cc3s2)cn1]

Embodiment 20 Synthesis of Target Compound 17r

Target Compound 17r is prepared by reactions with Intermediate 11s, wherein the ratio of raw materials, the solvents and the reaction conditions are the same as that of Embodiment 13, and the yield rate is 35.7%. $^1$H NMR (400 MHz, CDCl$_3$) δ8.76 (s, 1H), 8.13 (d, J=8.9 Hz, 1H), 7.87 (d, J=8.9 Hz, 1H), 7.35 (d, J=1.9 Hz, 1H), 7.06 (dd, J=8.8, 1.9 Hz, 1H), 6.59 (d, J=9.0 Hz, 1H), 4.73-4.65 (m, 1H), 4.61-4.53 (m, 1H), 4.34-4.26 (m, 1H), 4.16-4.11 (m, 2H), 3.19 (s, 6H), HRMS(EI): m/z calcd for C$_{17}$H$_{19}$N$_3$O$_2$FS 348.1182. found 348.1189 (M+H)$^+$.

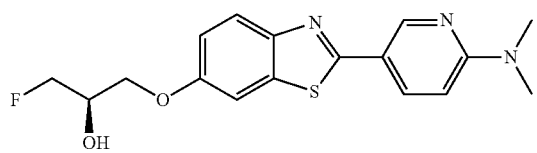 [SMILES: CN(C)c1ccc(-c2nc3ccc(OC[C@@H](O)CF)cc3s2)cn1]

Embodiment 21 Synthesis of Target Compound 18s

Target Compound 18s is prepared by reactions with Intermediate 12r, wherein the ratio of raw materials, the solvents and the reaction conditions are the same as that of Embodiment 13, and the yield rate is 62.4%. $^1$H NMR (400 MHz, CDCl$_3$) δ8.06 (d, J=8.7 Hz, 2H), 7.59 (d, J=8.7 Hz, 1H), 7.08 (d, J=2.3 Hz, 1H), 6.93 (dd, J=8.7, 2.4 Hz, 1H), 6.77 (d, J=8.4 Hz, 2H), 4.75-4.64 (m, 1H), 4.63-4.52 (m, 1H), 4.39-4.25 (m, 1H), 4.19-4.01 (m, 2H), 2.94 (s, 3H).

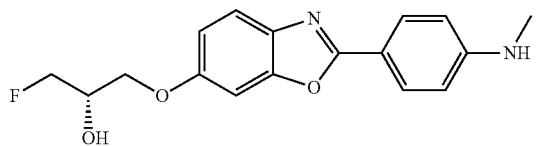 [SMILES: CNc1ccc(-c2nc3ccc(OC[C@H](O)CF)cc3o2)cc1]

Embodiment 22 Synthesis of Target Compound 18r

Target Compound 18r is prepared by reactions with Intermediate 12s, wherein the ratio of raw materials, the solvents and the reaction conditions are the same as that of Embodiment 13, and the yield rate is 51.4%. $^1$H NMR (400 MHz, CDCl$_3$) δ8.03 (d, J=8.8 Hz, 2H), 7.57 (d, J=8.7 Hz, 1H), 7.09 (d, J=2.3 Hz, 1H), 6.91 (dd, J=8.7, 2.4 Hz, 1H), 6.68 (d, J=8.6 Hz, 2H), 4.75-4.64 (m, 1H), 4.63-4.52 (m, 1H), 4.38-4.24 (m, 1H), 4.19-4.06 (m, 2H), 2.92 (s, 3H).

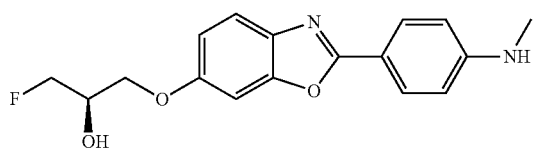 [SMILES: CNc1ccc(-c2nc3ccc(OC[C@@H](O)CF)cc3o2)cc1]

Embodiment 23 Synthesis of Target Compound 19s

Target Compound 19s is prepared by reactions with Intermediate 13r, wherein the ratio of raw materials, the solvents and the reaction conditions are the same as that of Embodiment 13, and the yield rate is 61.1%. $^1$H NMR (400 MHz, CDCl$_3$) δ8.07 (d, J=8.9 Hz, 2H), 7.58 (d, J=8.7 Hz, 1H), 7.10 (d, J=2.3 Hz, 1H), 6.92 (dd, J=8.7, 2.4 Hz, 1H), 6.78 (d, J=8.8 Hz, 2H), 4.73-4.65 (m, 1H), 4.62-4.53 (m, 1H), 4.38-4.22 (m, 1H), 4.17-4.07 (m, 1H), 3.08 (s, 6H).

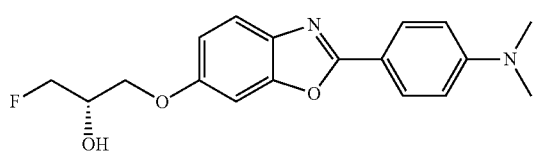 [SMILES: CN(C)c1ccc(-c2nc3ccc(OC[C@H](O)CF)cc3o2)cc1]

Embodiment 24 Synthesis of Target Compound 19r

Target Compound 19r is prepared by reactions with Intermediate 13s, wherein the ratio of raw materials, the solvents and the reaction conditions are the same as that of Embodiment 13, and the yield rate is 63.3%. $^1$H NMR (400 MHz, CDCl$_3$) δ8.06 (d, J=8.5 Hz, 2H), 7.58 (d, J=8.7 Hz, 1H), 7.10 (d, J=2.3 Hz, 1H), 6.92 (dd, J=8.7, 2.4 Hz, 1H), 6.78 (d, J=7.9 Hz, 2H), 4.73-4.65 (m, 1H), 4.62-4.53 (m, 1H), 4.40-4.22 (m, 1H), 4.19-4.06 (m, 1H), 4.17-4.09 (m, 1H), 3.07 (s, 6H).

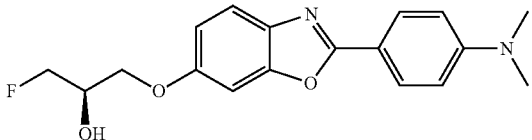

Embodiment 25 Synthesis of Intermediate 24r

Intermediate 24r is prepared by reactions with Compound 20, wherein the ratio of the raw material, the solvents and the reaction conditions are the same as that of Embodiment 1, and the yield rate is 31.7%. $^1$H NMR (400 MHz, CDCl$_3$) δ8.06 (d, J=8.8 Hz, 2H), 7.40 (d, J=8.8 Hz, 1H), 7.21 (d, J=2.5 Hz, 1H), 6.91 (dd, J=8.8, 2.5 Hz, 1H), 6.67 (d, J=8.8 Hz, 2H), 4.27 (dd, J=10.9, 3.2 Hz, 1H), 4.01 (dd, J=10.9, 5.7 Hz, 1H), 3.42-3.37 (m, 1H), 2.93 (s, 3H), 2.94-2.91 (m, 1H), 2.79 (dd, J=4.9, 2.6 Hz, 1H), MS(ESI): m/z calcd for C$_{17}$H$_{16}$N$_2$O$_3$ 296.12. found 297.2 (M+H)$^+$.

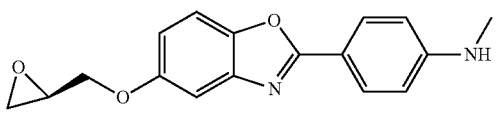 [SMILES: CNc1ccc(-c2nc3cc(OC[C@H]4CO4)ccc3o2)cc1]

Embodiment 26 Synthesis of Intermediate 24s

Intermediate 24s is prepared by reactions with Compound 20, wherein the ratio of the raw material, the solvents and the reaction conditions are the same as that of Embodiment 1, and the yield rate is 16.2%. $^1$H NMR (400 MHz, CDCl$_3$) δ8.04 (d, J=8.8 Hz, 2H), 7.39 (d, J=8.8 Hz, 1H), 7.20 (d, J=2.4 Hz, 1H), 6.90 (dd, J=8.8, 2.5 Hz, 1H), 6.66 (d, J=8.8 Hz, 2H), 4.26 (dd, J=10.9, 3.2 Hz, 1H), 4.00 (dd, J=10.9, 5.7 Hz, 1H), 3.42-3.37 (m, 1H), 2.92 (s, 3H), 2.94-2.90 (m, 1H), 2.79 (dd, J=4.9, 2.7 Hz, 1H), MS(ESI): m/z calcd for C$_{17}$H$_{16}$N$_2$O$_3$ 296.12. found 297.2 (M+H)$^+$.

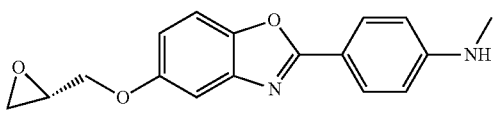

Embodiment 27 Synthesis of Intermediate 25r

Intermediate 25r is prepared by reactions with Compound 21, wherein the ratio of the raw material, the solvents and the reaction conditions are the same as that of Embodiment 1, and the yield rate is 52.9%. $^1$H NMR (400 MHz, CDCl$_3$) δ8.08 (d, J=9.0 Hz, 2H), 7.39 (d, J=8.8 Hz, 1H), 7.21 (d, J=2.4 Hz, 1H), 6.90 (dd, J=8.8, 2.5 Hz, 1H), 6.76 (d, J=9.0 Hz, 2H), 4.26 (dd, J=10.9, 3.2 Hz, 1H), 4.01 (dd, J=10.9, 5.6 Hz, 1H), 3.42-3.37 (m, 1H), 3.07 (s, 6H), 2.92 (t, J=4.5 Hz, 1H), 2.79 (dd, J=4.9, 2.6 Hz, 1H), MS(ESI): m/z calcd for C$_{18}$H$_{18}$N$_2$O$_3$ 310.13. found 311.2 (M+H)$^+$.

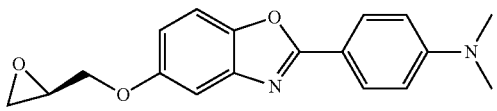 [SMILES: CN(C)c1ccc(-c2nc3cc(OC[C@H]4CO4)ccc3o2)cc1]

Embodiment 28 Synthesis of Intermediate 25s

Intermediate 25s is prepared by reactions with Compound 21, wherein the ratio of the raw material, the solvents and the reaction conditions are the same as that of Embodiment 1, and the yield rate is 72.9%. $^1$H NMR (400 MHz, CDCl$_3$) δ8.08 (d, J=9.0 Hz, 2H), 7.39 (d, J=8.8 Hz, 1H), 7.21 (d, J=2.4 Hz, 1H), 6.90 (dd, J=8.8, 2.5 Hz, 1H), 6.76 (d, J=9.0 Hz, 2H), 4.26 (dd, J=10.9, 3.2 Hz, 1H), 4.01 (dd, J=10.9, 5.6 Hz, 1H), 3.42-3.37 (m, 1H), 3.07 (s, 6H), 2.92 (t, J=4.5 Hz, 1H), 2.79 (dd, J=4.9, 2.6 Hz, 1H), MS(ESI): m/z calcd for C$_{18}$H$_{18}$N$_2$O$_3$ 310.13. found 311.2 (M+H)$^+$.

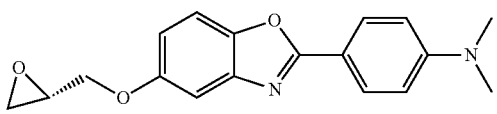 [SMILES: CN(C)c1ccc(-c2nc3cc(OC[C@@H]4CO4)ccc3o2)cc1]

Embodiment 29 Synthesis of Intermediate 26r

Intermediate 26r is prepared by reactions with Compound 22, wherein the ratio of the raw material, the solvents and the reaction conditions are the same as that of Embodiment 1, and the yield rate is 34.6%. $^1$H NMR (400 MHz, CDCl$_3$) δ8.93 (d, J=2.0 Hz, 1H), 8.22 (dd, J=8.8, 2.2 Hz, 1H), 7.42 (d, J=8.8 Hz, 1H), 7.21 (d, J=2.4 Hz, 1H), 6.93 (dd, J=8.8, 2.5 Hz, 1H), 6.50 (d, J=8.8 Hz, 1H), 5.18 (s, 1H), 4.28 (dd, J=10.9, 3.1 Hz, 1H), 4.00 (dd, J=10.9, 5.7 Hz, 1H), 3.43-3.38 (m, 1H), 3.02 (d, J=5.1 Hz, 3H), 2.94 (t, J=4.5 Hz, 1H), 2.80 (dd, J=4.9, 2.6 Hz, 1H), MS(ESI): m/z calcd for C$_{16}$H$_{15}$N$_3$O$_3$ 297.11. found 298.2 (M+H)$^+$.

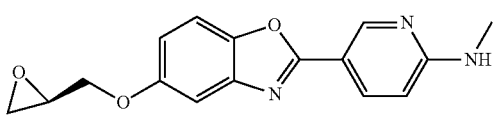 [SMILES: CNc1ccc(-c2nc3cc(OC[C@H]4CO4)ccc3o2)cn1]

Embodiment 30 Synthesis of Intermediate 26s

Intermediate 26s is prepared by reactions with Compound 22, wherein the ratio of the raw material, the solvents and the reaction conditions are the same as that of Embodiment 1, and the yield rate is 33.3%. $^1$H NMR (400 MHz, CDCl$_3$) δ8.93 (d, J=1.6 Hz, 1H), 8.22 (dd, J=8.8, 2.1 Hz, 1H), 7.42 (d, J=8.8 Hz, 1H), 7.21 (d, J=2.4 Hz, 1H), 6.93 (dd, J=8.8, 2.5 Hz, 1H), 6.50 (d, J=8.9 Hz, 1H), 5.19 (s, 1H), 4.28 (dd, J=10.9, 3.1 Hz, 1H), 4.00 (dd, J=10.9, 5.7 Hz, 1H), 3.42-3.39 (m, 1H), 3.02 (d, J=5.1 Hz, 3H), 2.94 (t, J=4.5 Hz, 1H), 2.80 (dd, J=4.9, 2.6 Hz, 1H), MS(ESI): m/z calcd for C$_{16}$H$_{15}$N$_3$O$_3$ 297.11. found 298.2 (M+H)$^+$.

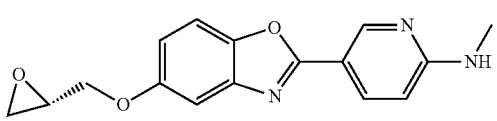 [SMILES: CNc1ccc(-c2nc3cc(OC[C@@H]4CO4)ccc3o2)cn1]

Embodiment 31 Synthesis of Intermediate 27r

Intermediate 27r is prepared by reactions with Compound 23, wherein the ratio of the raw material, the solvents and the reaction conditions are the same as that of Embodiment 1, and the yield rate is 71.7%. $^1$H NMR (400 MHz, CDCl$_3$) δ8.98 (d, J=2.2 Hz, 1H), 8.21 (d, J=9.0 Hz, 1H), 7.42 (d, J=8.8 Hz, 1H), 7.21 (d, J=2.4 Hz, 1H), 6.92 (dd, J=8.8, 2.5 Hz, 1H), 6.61 (d, J=9.0 Hz, 1H), 4.28 (dd, J=10.9, 3.1 Hz, 1H), 4.00 (dd, J=10.9, 5.7 Hz, 1H), 3.43-3.38 (m, 1H), 3.21 (s, 6H), 2.93 (t, J=4.5 Hz, 1H), 2.80 (dd, J=4.9, 2.6 Hz, 1H), MS(ESI): m/z calcd for C$_{17}$H$_{17}$N$_3$O$_3$311.13. found 312.2 (M+H)$^+$.

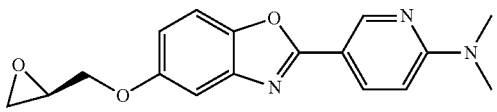 [SMILES: CN(C)c1ccc(-c2nc3cc(OC[C@H]4CO4)ccc3o2)cn1]

Embodiment 32 Synthesis of Intermediate 27s

Intermediate 27s is prepared by reactions with Compound 23, wherein the ratio of the raw material, the solvents and the reaction conditions are the same as that of Embodiment 1, and the yield rate is 61.8%. 1H NMR (400 MHz, CDCl$_3$) δ8.87 (d, J=2.1 Hz, 1H), 8.09 (dd, J=8.9, 1.9 Hz, 1H), 7.31 (d, J=8.8 Hz, 1H), 7.09 (d, J=2.4 Hz, 1H), 6.81 (dd, J=8.8, 2.5 Hz, 1H), 6.49 (d, J=9.0 Hz, 1H), 4.17 (dd, J=10.9, 3.1 Hz, 1H), 3.88 (dd, J=10.9, 5.7 Hz, 1H), 3.32-3.27 (m, 1H), 3.09 (s, 6H), 2.82 (t, J=4.5 Hz, 1H), 2.69 (dd, J=4.8, 2.6 Hz, 1H), MS(ESI): m/z calcd for C$_{17}$H$_{17}$N$_3$O$_3$311.13. found 312.2 (M+H)$^+$.

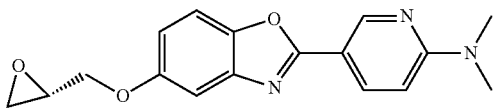 [SMILES: CN(C)c1ccc(-c2nc3cc(OC[C@@H]4CO4)ccc3o2)cn1]

Embodiment 33 Synthesis of Target Compound 28s

Target Compound 28s is prepared by reactions with Intermediate 24r, wherein the ratio of raw materials, the solvents and the reaction conditions are the same as that of Embodiment 13, and the yield rate is 16.6%. $^1$H NMR (400 MHz, CDCl$_3$) δ8.05 (d, J=8.6 Hz, 2H), 7.40 (d, J=8.8 Hz, 1H), 7.22 (d, J=2.1 Hz, 1H), 6.88 (dd, J=8.8, 2.1 Hz, 1H), 6.67 (d, J=8.6 Hz, 2H), 4.73-4.64 (m, 1H), 4.61-4.52 (m, 1H), 4.34-4.24 (m, 1H), 4.16-4.09 (m, 2H), 2.93 (s, 3H), HRMS(EI): m/z calcd for C$_{17}$H$_{18}$N$_2$O$_3$F 317.1301. found 317.1293 (M+H)$^+$.

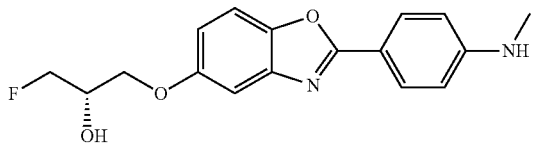 [SMILES: CNc1ccc(-c2nc3cc(OC[C@H](O)CF)ccc3o2)cc1]

Embodiment 34 Synthesis of Target Compound 28r

Target Compound 28r is prepared by reactions with Intermediate 24s, wherein the ratio of raw materials, the solvents and the reaction conditions are the same as that of Embodiment 13, and the yield rate is 31.3%. $^1$H NMR (400 MHz, CDCl$_3$) δ8.05 (d, J=8.7 Hz, 2H), 7.40 (d, J=8.8 Hz, 1H), 7.22 (d, J=2.5 Hz, 1H), 6.88 (dd, J=8.8, 2.5 Hz, 1H), 6.67 (d, J=8.8 Hz, 2H), 4.72-4.64 (m, 1H), 4.60-4.52 (m, 1H), 4.34-4.24 (m, 1H), 4.16-4.07 (m, 2H), 2.92 (s, 3H). HRMS(EI): m/z calcd for C$_{17}$H$_{18}$N$_2$O$_3$F 317.1301. found 317.1295 (M+H)$^+$.

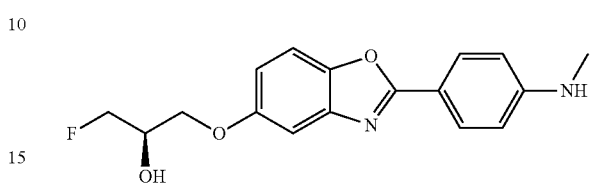

Embodiment 35 Synthesis of Target Compound 29s

Target Compound 29s is prepared by reactions with Intermediate 25r, wherein the ratio of raw materials, the solvents and the reaction conditions are the same as that of Embodiment 13, and the yield rate is 53.0%. $^1$H NMR (400 MHz, CDCl$_3$) δ8.08 (d, J=8.5 Hz, 2H), 7.40 (d, J=8.6 Hz, 1H), 7.22 (s, 1H), 6.87 (d, J=8.0 Hz, 1H), 6.77 (d, J=8.3 Hz, 2H), 4.68-4.66 (m, 1H), 4.57-4.54 (m, 1H), 4.32-4.27 (m, 1H), 4.13 (s, 2H), 3.07 (s, 6H), HRMS(EI): m/z calcd for C$_{18}$H$_{20}$N$_2$O$_3$F 331.1458. found 331.1448 (M+H)$^+$.

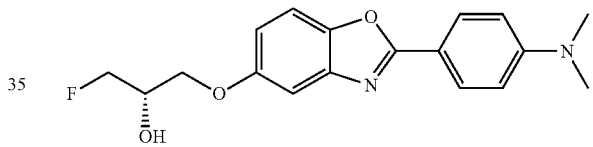

Embodiment 36 Synthesis of Target Compound 29r

Target Compound 29r is prepared by reactions with Intermediate 25s, wherein the ratio of raw materials, the solvents and the reaction conditions are the same as that of Embodiment 13, and the yield rate is 28.0%. $^1$H NMR (400 MHz, CDCl$_3$) δ8.09 (d, J=8.6 Hz, 2H), 7.40 (d, J=8.8 Hz, 1H), 7.22 (s, 1H), 6.88 (d, J=8.7 Hz, 1H), 6.78 (d, J=8.6 Hz, 2H), 4.72-4.64 (m, 1H), 4.60-4.52 (m, 1H), 4.33-4.25 (m, 1H), 4.13 (s, 2H), 3.08 (s, 6H), HRMS(EI): m/z calcd for C$_{18}$H$_{20}$N$_2$O$_3$F 331.1458. found 331.1454 (M+H)$^+$.

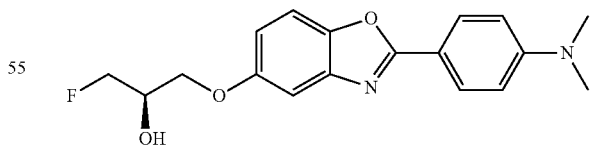

Embodiment 37 Synthesis of Target Compound 30s

Target Compound 30s is prepared by reactions with Intermediate 26r, wherein the ratio of raw materials, the solvents and the reaction conditions are the same as that of Embodiment 13, and the yield rate is 22.6%. $^1$H NMR (400 MHz, CDCl$_3$) δ8.92 (d, J=1.6 Hz, 1H), 8.23 (dd, J=8.8, 1.7

Hz, 1H), 7.43 (d, J=8.8 Hz, 1H), 7.22 (d, J=2.3 Hz, 1H), 6.91 (dd, J=8.8, 2.3 Hz, 1H), 6.51 (d, J=8.9 Hz, 1H), 5.26 (s, 1H), 4.74-4.65 (m, 1H), 4.62-4.54 (m, 1H), 4.34-4.27 (m, 1H), 4.14-4.12 (m, 2H), 3.02 (d, J=5.1 Hz, 3H), HRMS(EI): m/z calcd for $C_{16}H_{17}N_3O_3F$ 318.1254. found 318.1251 (M+H)+.

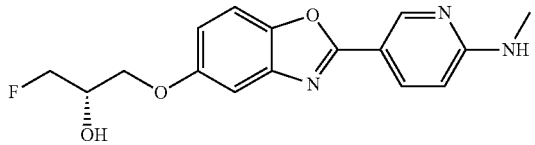

Embodiment 38 Synthesis of Target Compound 30r

Target Compound 30r is prepared by reactions with Intermediate 26s, wherein the ratio of raw materials, the solvents and the reaction conditions are the same as that of Embodiment 13, and the yield rate is 28.2%. $^1$H NMR (400 MHz, CDCl$_3$) δ8.93 (s, 1H), 8.21 (d, J=8.8 Hz, 1H), 7.42 (d, J=8.8 Hz, 1H), 7.21 (d, J=2.0 Hz, 1H), 6.90 (dd, J=8.8, 2.2 Hz, 1H), 6.49 (d, J=8.8 Hz, 1H), 5.09 (s, 1H), 4.73-4.64 (m, 1H), 4.61-4.52 (m, 1H), 4.35-4.24 (m, 1H), 4.13 (s, 2H), 3.01 (d, J=5.1 Hz, 3H), HRMS(EI): m/z calcd for $C_{16}H_{17}N_3O_3F$ 318.1254. found 318.1246 (M+H)+.

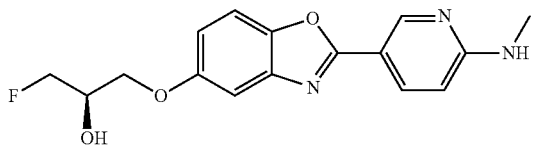 [SMILES: CNc1ccc(-c2nc3cc(OC[C@@H](O)CF)ccc3o2)cn1]

Embodiment 39 Synthesis of Target Compound 31s

Target Compound 31s is prepared by reactions with Intermediate 27r, wherein the ratio of raw materials, the solvents and the reaction conditions are the same as that of Embodiment 13, and the yield rate is 19.5%. $^1$H NMR (400 MHz, CDCl$_3$) δ8.98 (d, J=1.8 Hz, 1H), 8.20 (dd, J=9.0, 2.0 Hz, 1H), 7.42 (d, J=8.8 Hz, 1H), 7.21 (d, J=2.3 Hz, 1H), 6.89 (dd, J=8.8, 2.3 Hz, 1H), 6.60 (d, J=9.0 Hz, 1H), 4.74-4.65 (m, 1H), 4.62-4.53 (m 1H), 4.35-4.26 (m, 1H), 4.16-4.09 (m, 2H), 3.20 (s, 6H), HRMS(EI): m/z calcd for $C_{17}H_{19}N_3O_3F$ 332.1410. found 332.1415 (M+H)+.

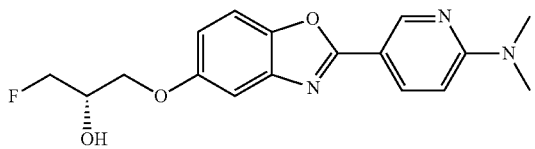 [SMILES: CN(C)c1ccc(-c2nc3cc(OC[C@H](O)CF)ccc3o2)cn1]

Embodiment 40 Synthesis of Target Compound 31r

Target Compound 31r is prepared by reactions with Intermediate 27s, wherein the ratio of raw materials, the solvents and the reaction conditions are the same as that of Embodiment 13, and the yield rate is 29.2%. $^1$H NMR (400 MHz, CDCl$_3$) δ9.00 (d, J=2.0 Hz, 1H), 8.23 (d, J=7.9 Hz, 1H), 7.44 (d, J=8.8 Hz, 1H), 7.23 (d, J=2.4 Hz, 1H), 6.92 (dd, J=8.8, 2.5 Hz, 1H), 6.64 (d, J=8.9 Hz, 1H), 4.75-4.66 (m, 1H), 4.63-4.55 (m, 1H), 4.37-4.27 (m, 1H), 4.18-4.11 (m, 2H), 3.23 (s, 6H), HRMS(EI): m/z calcd for $C_{17}H_{19}N_3O_3F$ 332.1410. found 332.1403 (M+H)+.

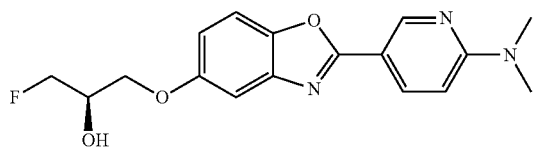 [SMILES: CN(C)c1ccc(-c2nc3cc(OC[C@@H](O)CF)ccc3o2)cn1]

Embodiment 41 Synthesis of Labeled Intermediate 33s

Dissolve Compound 20 (240.0 mg, 1 mmol) in 20 mL of ethanol. Add a NaOH solution (69.0 mg, 2 mL) to the mixture. Stir the mixture in an oil bath at 80° C. until reflux has occurred for 1 h. Add Compound 32s (135.5 mg, 1.2 mmol) to the mixture and keep stirring the mixture until reflux has occurred for 3 h. After the reactions are completed, separate the mixture by the column chromatography to obtain 146.0 mg of Intermediate 33s with a yield rate of 46.5%. $^1$H NMR (400 MHz, d$_6$-DMSO) δ7.90 (d, J=7.9 Hz, 2H), 7.55 (d, J=8.2 Hz, 1H), 7.20 (s, 1H), 6.89 (d, J=8.7 Hz, 1H), 6.68 (d, J=7.9 Hz, 2H), 6.55 (s, 1H), 4.96 (d, J=3.4 Hz, 1H), 4.68 (s, 1H), 4.03 (s, 1H), 3.97-3.85 (m, 1H), 3.82 (s, 1H), 3.47 (s, 2H), 2.76 (d, J=2.7 Hz, 3H), MS(ESI): m/z calcd for $C_{17}H_{18}N_2O_4$ 314.13. found 315.2 (M+H)+.

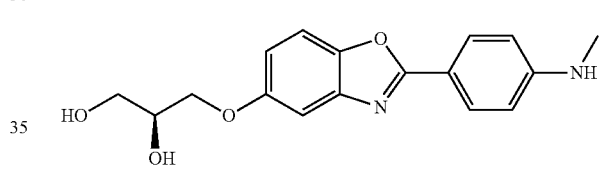

Embodiment 42 Synthesis of Labeled Intermediate 33r

Intermediate 33r is prepared by reactions with Compound 20, wherein the ratio of the raw material, the solvents and the reaction conditions are the same as that of Embodiment 41, and the yield rate is 39.6%. $^1$H NMR (400 MHz, d$_6$-DMSO) δ7.90 (d, J=8.8 Hz, 2H), 7.54 (d, J=8.8 Hz, 1H), 7.20 (d, J=2.5 Hz, 1H), 6.88 (dd, J=8.8, 2.5 Hz, 1H), 6.67 (d, J=8.8 Hz, 2H), 6.53 (d, J=5.0 Hz, 1H), 4.04 (dd, J=9.9, 4.2 Hz, 1H), 3.91 (dd, J=9.9, 6.1 Hz, 1H), 3.82 (dd, J=10.7, 5.0 Hz, 1H), 3.47 (d, J=5.7 Hz, 2H), 2.76 (d, J=4.1 Hz, 3H), MS(ESI): m/z calcd for $C_{17}H_{18}N_2O_4$ 314.13. found 315.3 (M+H)+.

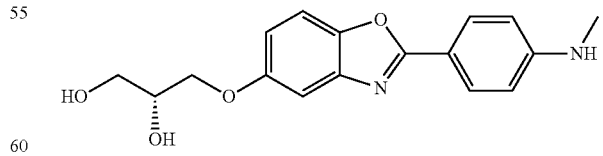

Embodiment 43 Synthesis of Labeled Intermediate 34r

Dissolve Compound 33s (129.0 mg, 0.4 mmol) in 30 mL of a CH$_2$Cl$_2$ solution. Add 1 mL of imidazole (237.9 mg, 3.5 mmol) and TBDMSCl (536.2 mg, 3.6 mmol) to the mixture. Stir the mixture in an oil bath at 40° C. until reflux occurs. After the reaction is completed, filter out deposits and remove CH$_2$Cl$_2$. Separate the remainder by the column chromatography to obtain 154.2 mg of Intermediate 34r with a yield rate of 71.1%. $^1$H NMR (400 MHz, CDCl$_3$) δ7.96 (d, J=8.7 Hz, 2H), 7.28 (d, J=8.8 Hz, 1H), 7.10 (d, J=2.4 Hz, 1H), 6.77 (dd, J=8.8, 2.5 Hz, 1H), 6.57 (d, J=8.8 Hz, 2H), 4.08-3.94 (m, 2H), 3.80 (dd, J=8.4, 5.6 Hz, 1H), 3.57 (d, J=5.7 Hz, 2H), 2.82 (s, 3H), 0.80 (s, 18H), MS(ESI): m/z calcd for C$_{29}$H$_{46}$N$_2$O$_4$Si$_2$542.30. found 543.7 (M+H)$^+$.

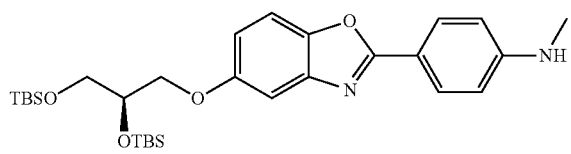 [SMILES: CNc1ccc(-c2nc3cc(OC[C@H](CO[Si](C)(C)C(C)(C)C)O[Si](C)(C)C(C)(C)C)ccc3o2)cc1]

Embodiment 44 Synthesis of Labeled Intermediate 34s

Intermediate 34s is prepared by reactions with Intermediate 33r, wherein the ratio of raw materials, the solvents and the reaction conditions are the same as that of Embodiment 43, and the yield rate is 24.2%. $^1$H NMR (400 MHz, CDCl$_3$) δ7.97 (d, J=8.8 Hz, 2H), 7.30 (d, J=8.8 Hz, 1H), 7.12 (d, J=2.4 Hz, 1H), 6.79 (dd, J=8.8, 2.5 Hz, 1H), 6.59 (d, J=8.8 Hz, 2H), 4.06-3.99 (m, 2H), 3.85-3.81 (m, 1H), 3.60 (d, J=5.7 Hz, 2H), 2.84 (s, 3H), 0.83 (s, 18H), MS(ESI): m/z calcd for C$_{29}$H$_{46}$N$_2$O$_4$Si$_2$542.30. found 543.1 (M+H)$^+$.

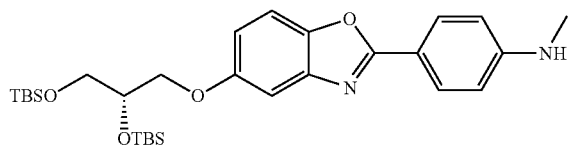 [SMILES: CNc1ccc(-c2nc3cc(OC[C@@H](CO[Si](C)(C)C(C)(C)C)O[Si](C)(C)C(C)(C)C)ccc3o2)cc1]

Embodiment 45 Synthesis of Labeled Intermediate 35r

Dissolve Compound 34r (245.7 mg, 0.45 mmol) in 30 mL of a THF solution. Add an excessive dose of (Boc)$_2$O to the mixture. Stir the mixture in an oil bath at 85° C. until reflux occurs. After the reaction is completed, filter out THF. Separate the remainder by the column chromatography to obtain 279.2 mg of Intermediate 35r with a yield rate of 95.9%. $^1$H NMR (400 MHz, CDCl$_3$) δ8.11 (d, J=8.5 Hz, 2H), 7.36 (t, J=8.6 Hz, 3H), 7.17 (d, J=2.3 Hz, 1H), 6.88 (dd, J=8.9, 2.2 Hz, 1H), 4.10-3.96 (m, 2H), 3.84 (dd, J=8.8, 6.2 Hz, 1H), 3.60 (d, J=5.8 Hz, 2H), 3.26 (s, 3H), 1.41 (s, 9H), 0.83 (s, 18H), MS(ESI): m/z calcd for C$_{34}$H$_{54}$N$_2$O$_6$Si$_2$642.35. found 643.6 (M+H)$^+$.

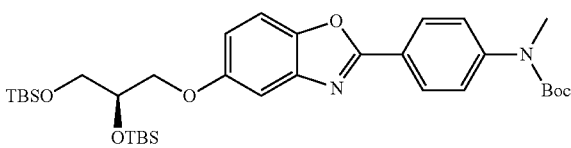 [SMILES: CN(C(=O)OC(C)(C)C)c1ccc(-c2nc3cc(OC[C@H](CO[Si](C)(C)C(C)(C)C)O[Si](C)(C)C(C)(C)C)ccc3o2)cc1]

Embodiment 46 Synthesis of Labeled Intermediate 35s

Intermediate 35s is prepared by reactions with Intermediate 34r, wherein the ratio of raw materials, the solvents and the reaction conditions are the same as that of Embodiment 45, and the yield rate is 88.0%. $^1$H NMR (400 MHz, CDCl$_3$) δ8.10 (d, J=8.7 Hz, 2H), 7.35 (t, J=8.7 Hz, 3H), 7.17 (d, J=2.4 Hz, 1H), 6.87 (dd, J=8.9, 2.5 Hz, 1H), 4.13-3.98 (m, 2H), 3.84 (dd, J=8.9, 6.2 Hz, 1H), 3.70-3.53 (m, 2H), 3.25 (s, 3H), 1.41 (s, 9H), 0.83 (s, 18H), MS(ESI): m/z calcd for C$_{34}$H$_{54}$N$_2$O$_6$Si$_2$642.35. found 643.4 (M+H)$^+$.

Embodiment 47 Synthesis of Labeled Intermediate 36s

Dissolve Compound 35r (273.2 mg, 0.37 mmol) in 20 mL of a THF solution. Add 2.5 mL of a THF solution containing TBAF to the mixture. Stir the mixture in an oil bath at 30° C. until reflux occurs. After the reaction is completed, filter out THF. Separate the remainder by the column chromatography to obtain 78.6 mg of Intermediate 36s with a yield rate of 37.4%. $^1$H NMR (400 MHz, CDCl$_3$) δ8.13 (d, J=8.5 Hz, 2H), 7.38 (dd, J=15.0, 8.7 Hz, 3H), 7.23 (d, J=2.2 Hz, 1H), 6.88 (dd, J=8.8, 2.4 Hz, 1H), 4.20-4.12 (m, 1H), 4.07 (s, 2H), 3.86 (dd, J=11.4, 3.5 Hz, 1H), 3.78 (dd, J=11.4, 5.7 Hz, 1H), 3.31 (d, J=2.7 Hz, 3H), 1.49 (s, 9H), MS(ESI): m/z calcd for C$_{22}$H$_{26}$N$_2$O$_6$ 414.18. found 415.3 (M+H)$^+$.

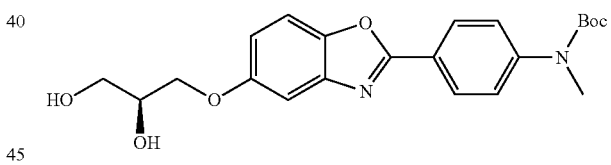

Embodiment 48 Synthesis of Labeled Intermediate 36r

Intermediate 36r is prepared by reactions with Intermediate 35s, wherein the ratio of raw materials, the solvents and the reaction conditions are the same as that of Embodiment 47, and the yield rate is 60.1%. $^1$H NMR (400 MHz, CDCl$_3$) δ8.17 (d, J=8.8 Hz, 2H), 7.43 (t, J=8.6 Hz, 3H), 7.25 (s, 1H), 6.94 (dd, J=8.8, 2.5 Hz, 1H), 4.21-4.13 (m, 1H), 4.13-4.05 (m, 2H), 3.87 (dd, J=11.4, 3.8 Hz, 1H), 3.79 (dd, J=11.4, 5.4 Hz, 1H), 3.33 (s, 3H), 1.49 (s, 9H).

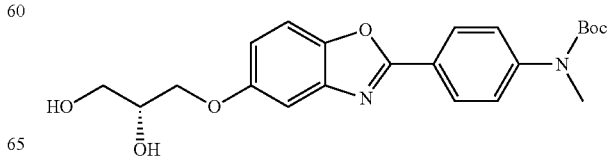

Embodiment 49 Synthesis of Labeled Intermediate 37r

Dissolve Compound 36s (79.6 mg, 0.19 mmol) in 5 mL of pyridine. Add TsCl (55.2 mg, 0.29 mmol) to the mixture. Stir the mixture in an ice bath at 0° C. until reflux occurs. After the reaction is completed, filter out the pyridine. Separate the remainder by the column chromatography to obtain 30.0 mg of Intermediate 37r with a yield rate of 27.8%. $^1$H NMR (400 MHz, CDCl$_3$) δ8.17 (t, J=5.6 Hz, 2H), 7.79 (d, J=8.2 Hz, 2H), 7.43 (d, J=8.7 Hz, 3H), 7.30 (d, J=8.1 Hz, 2H), 7.15 (d, J=2.4 Hz, 1H), 6.86 (dd, J=8.9, 2.5 Hz, 1H), 4.34-4.13 (m, 3H), 4.03 (d, J=4.3 Hz, 2H), 3.33 (s, 3H), 2.40 (s, 3H), 1.49 (s, 9H), MS(ESI): m/z calcd for C$_{29}$H$_{32}$N$_2$O$_8$S 568.19. found 569.6 (M+H)$^+$.

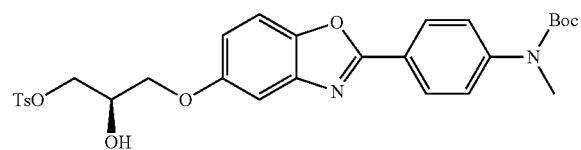 [SMILES: Cc1ccc(S(=O)(=O)OC[C@H](O)COc2ccc3oc(-c4ccc(N(C)C(=O)OC(C)(C)C)cc4)nc3c2)cc1]

Embodiment 50 Synthesis of Labeled Intermediate 37s

Intermediate 37s is prepared by reactions with Intermediate 36r, wherein the ratio of raw materials, the solvents and the reaction conditions are the same as that of Embodiment 49, and the yield rate is 62.3%. $^1$H NMR (400 MHz, CDCl$_3$) δ8.18 (d, J=8.7 Hz, 2H), 7.81 (d, J=8.2 Hz, 2H), 7.44 (dd, J=8.7, 3.8 Hz, 3H), 7.32 (d, J=8.0 Hz, 2H), 7.16 (d, J=2.3 Hz, 1H), 6.87 (dd, J=8.9, 2.4 Hz, 1H), 4.34-4.20 (m, 3H), 4.04 (d, J=4.1 Hz, 2H), 3.34 (s, 3H), 2.41 (s, 3H), 1.49 (s, 9H).

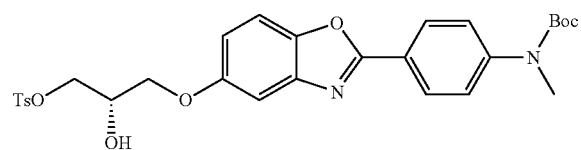 [SMILES: Cc1ccc(S(=O)(=O)OC[C@@H](O)COc2ccc3oc(-c4ccc(N(C)C(=O)OC(C)(C)C)cc4)nc3c2)cc1]

Embodiment 51 Synthesis of Labeled Precursor 38r

Dissolve Compound 37r (30.0 mg, 0.05 mmol) in 10 mL of a CH$_2$Cl$_2$ solution. Add 3, 4-dihydro-2H-pyran (78.2 mg, 0.93 mmol) and PPTS (59.2 mg, 0.24 mmol) to the mixture. Stir the mixture in an oil bath at 40° C. until reflux occurs. After the reaction is completed, Remove CH$_2$Cl$_2$ and separate the remainder by the column chromatography to obtain 19.9 mg of Labeled Precursor 38r with a yield rate of 61.0%. $^1$H NMR (400 MHz, CDCl$_3$) δ8.18 (d, J=8.5 Hz, 2H), 7.78 (dd, J=8.2, 5.5 Hz, 2H), 7.42 (dd, J=8.7, 3.3 Hz, 3H), 7.33-7.25 (m, 2H), 7.13 (dd, J=8.5, 2.4 Hz, 1H), 6.83 (ddd, J=8.8, 3.8, 2.6 Hz, 1H), 4.78 (dt, J=6.8, 3.8 Hz, 1H), 4.43-4.18 (m, 3H), 4.18-3.96 (m, 2H), 3.95-3.69 (m, 1H), 3.58-3.41 (m, 1H), 3.33 (s, 3H), 2.38 (s, 3H), 1.88-1.62 (m, 3H), 1.49 (s, 9H), MS(ESI): m/z calcd for C$_{34}$H$_{40}$N$_2$O$_9$S 652.25. found 653.6 (M+H)$^+$.

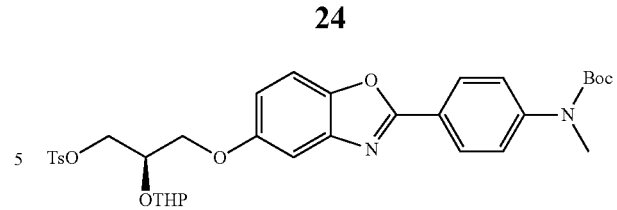

Embodiment 52 Synthesis of Labeled Precursor 38s

Labeled Precursor 38s is prepared by reactions with Intermediate 37s, wherein the ratio of raw materials, the solvents and the reaction conditions are the same as that of Embodiment 51, and the yield rate is 79.4%. $^1$H NMR (400 MHz, CDCl$_3$) δ8.18 (d, J=8.5 Hz, 2H), 7.78 (dd, J=8.2, 5.4 Hz, 2H), 7.42 (dd, J=8.6, 2.9 Hz, 3H), 7.28 (s, 2H), 7.13 (dd, J=8.4, 2.4 Hz, 1H), 6.89-6.80 (m, 1H), 4.86-4.69 (m, 1H), 4.42-4.17 (m, 3H), 4.12-3.96 (m, 2H), 4.00-3.76 (m, 1H), 3.51-3.47 (m, 1H), 3.33 (s, 3H), 2.39 (d, J=1.4 Hz, 3H), 1.87-1.63 (m, 3H), 1.64-1.52 (m, 3H), 1.49 (s, 9H).

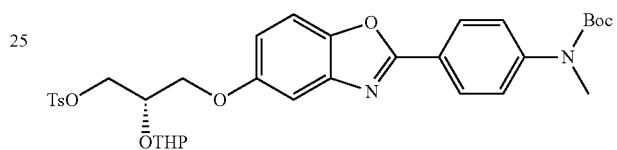

Embodiment 53 Synthesis of Labeled Intermediate 39s

Intermediate 39s is prepared by reactions with Compound 1 and Compound 32s, wherein the ratio of raw materials, the solvents and the reaction conditions are the same as that of Embodiment 41, and the yield rate is 80.9%. $^1$H NMR (400 MHz, d$_6$-DMSO) δ7.77 (t, J=8.6 Hz, 3H), 7.60 (d, J=2.5 Hz, 1H), 7.05 (dd, J=8.9, 2.5 Hz, 1H), 6.64 (d, J=8.8 Hz, 2H), 6.39 (d, J=4.9 Hz, 1H), 4.98 (d, J=5.1 Hz, 1H), 4.68 (t, J=5.6 Hz, 1H), 4.07 (dd, J=9.8, 4.2 Hz, 1H), 3.94 (dd, J=9.9, 6.1 Hz, 1H), 3.88-3.76 (m, 1H), 3.47 (t, J=5.7 Hz, 2H), 2.75 (d, J=4.9 Hz, 3H), MS(ESI): m/z calcd for C$_{17}$H$_{18}$N$_2$O$_3$S 330.10. found 330.8 (M+H)$^+$.

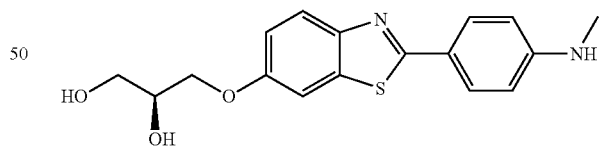

Embodiment 54 Synthesis of Labeled Intermediate 39r

Intermediate 39r is prepared by reactions with Compound 1 and Compound 32r, wherein the ratio of the raw material, the solvents and the reaction conditions are the same as that of Embodiment 41, and the yield rate is 49.0%. $^1$H NMR (400 MHz, d$_6$-DMSO) δ 7.78 (t, J=8.7 Hz, 3H), 7.60 (d, J=2.5 Hz, 1H), 7.05 (dd, J=8.8, 2.5 Hz, 1H), 6.63 (d, J=8.8 Hz, 2H), 6.38 (d, J=4.9 Hz, 1H), 4.97 (s, 1H), 4.68 (s, 1H), 4.07 (dd, J=9.9, 4.2 Hz, 1H), 3.94 (dd, J=9.9, 6.1 Hz, 1H), 3.84-3.81 (m, 1H), 3.47 (d, J=5.5 Hz, 2H), 2.75 (d, J=4.9 Hz, 3H), MS(ESI): m/z calcd for $C_{17}H_{18}N_2O_3S$ 330.10. found 330.8 (M+H)$^+$.

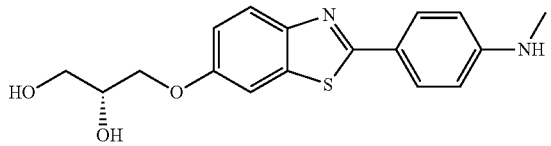

Embodiment 55 Synthesis of Labeled Intermediate 40r

Intermediate 40r is prepared by reactions with Intermediate 39s, wherein the ratio of raw materials, the solvents and the reaction conditions are the same as that of Embodiment 43, and the yield rate is 63.8%. $^1$H NMR (400 MHz, CDCl$_3$) δ7.84-7.75 (m, 3H), 7.22 (d, J=2.5 Hz, 1H), 6.95 (dd, J=8.9, 2.5 Hz, 1H), 6.55 (d, J=8.7 Hz, 2H), 4.11-4.01 (m, 1H), 4.03-3.94 (m, 1H), 3.83 (dd, J=9.5, 6.5 Hz, 1H), 3.63-3.51 (m, 2H), 2.81 (s, 3H), 0.81 (s, 9H), 0.80 (s, 9H), MS(ESI): m/z calcd for $C_{29}H_{46}N_2O_3SSi_2$ 558.28. found 559.1 (M+H)$^+$.

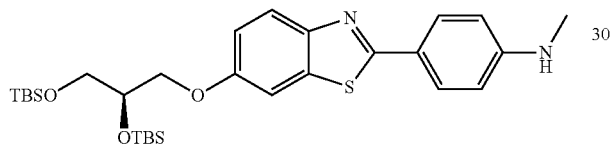

Embodiment 56 Synthesis of Labeled Intermediate 40s

Intermediate 40s is prepared by reactions with Intermediate 39r, wherein the ratio of raw materials, the solvents and the reaction conditions are the same as that of Embodiment 43, and the yield rate is 90.4%. $^1$H NMR (400 MHz, CDCl$_3$) δ7.81 (d, J=8.3 Hz, 3H), 7.24 (d, J=2.4 Hz, 1H), 6.97 (dd, J=8.9, 2.5 Hz, 1H), 6.57 (d, J=8.6 Hz, 2H), 4.08 (dd, J=9.5, 3.6 Hz, 1H), 4.03-3.97 (m, 1H), 3.86 (dd, J=9.5, 6.5 Hz, 1H), 3.65-3.51 (m, 2H), 2.83 (s, 3H), 0.83 (s, 9H), 0.82 (s, 9H), MS(ESI): m/z calcd for $C_{29}H_{46}N_2O_3SSi_2$ 558.28. found 559.0 (M+H)$^+$.

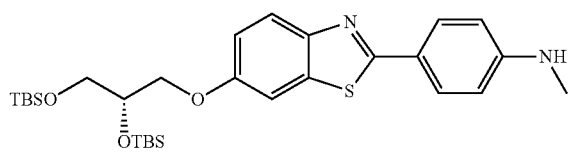 [SMILES: CNc1ccc(-c2nc3ccc(OC[C@@H](CO[Si](C)(C)C(C)(C)C)O[Si](C)(C)C(C)(C)C)cc3s2)cc1]

Embodiment 57 Synthesis of Labeled Intermediate 41r

Labeled Intermediate 41r is prepared by reactions with Intermediate 40r, wherein the ratio of raw materials, the solvents and the reaction conditions are the same as that of Embodiment 45, and the yield rate is 86.0%. $^1$H NMR (400 MHz, CDCl$_3$) δ7.92 (d, J=8.6 Hz, 2H), 7.86 (d, J=8.9 Hz, 1H), 7.29 (d, J=8.6 Hz, 3H), 7.02 (dd, J=8.9, 2.5 Hz, 1H), 4.10 (dd, J=9.5, 3.5 Hz, 1H), 4.06-3.97 (m, 1H), 3.87 (dd, J=9.5, 6.6 Hz, 1H), 3.65-3.52 (m, 2H), 3.24 (s, 3H), 1.40 (s, 9H), 0.83 (s, 9H), 0.82 (s, 9H), MS(ESI): m/z calcd for $C_{34}H_{54}N_2O_5SSi_2$ 658.33. found 659.37 (M+H)$^+$.

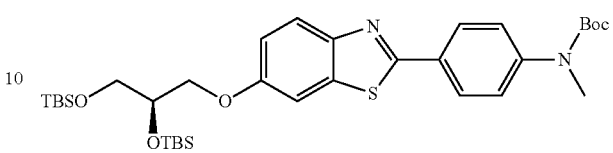

Embodiment 58 Synthesis of Labeled Intermediate 41s

Intermediate 41s is prepared by reactions with Intermediate 40s, wherein the ratio of raw materials, the solvents and the reaction conditions are the same as that of Embodiment 45, and the yield rate is 92.9%. $^1$H NMR (400 MHz, CDCl$_3$) δ7.91 (d, J=8.6 Hz, 2H), 7.85 (d, J=8.9 Hz, 1H), 7.33-7.25 (m, 3H), 7.01 (dd, J=9.0, 2.5 Hz, 1H), 4.10 (dd, J=9.5, 3.5 Hz, 1H), 4.07-3.96 (m, 1H), 3.87 (dd, J=9.5, 6.5 Hz, 1H), 3.66-3.49 (m, 2H), 3.23 (s, 3H), 1.40 (s, 9H), 0.83 (s, 9H), 0.82 (s, 9H), MS(ESI): m/z calcd for $C_{34}H_{54}N_2O_5SSi_2$ 658.33. found 659.1 (M+H)$^+$.

Embodiment 59 Synthesis of Labeled Intermediate 42s

Intermediate 42s is prepared by reactions with Intermediate 41r, wherein the ratio of raw materials, the solvents and the reaction conditions are the same as that of Embodiment 47, and the yield rate is 83.4%. $^1$H NMR (400 MHz, CDCl$_3$) δ8.01 (d, J=8.6 Hz, 2H), 7.96 (d, J=8.9 Hz, 1H), 7.43-7.34 (m, 3H), 7.10 (dd, J=8.9, 2.5 Hz, 1H), 4.22-4.09 (m, 3H), 3.88 (dd, J=11.4, 3.7 Hz, 1H), 3.79 (dd, J=11.4, 5.1 Hz, 1H), 3.32 (s, 3H), 1.49 (s, 9H), MS(ESI): m/z calcd for $C_{22}H_{26}N_2O_5S$ 430.16. found 431.20 (M+H)$^+$.

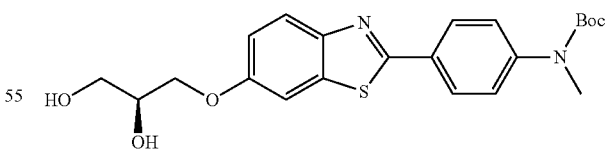

Embodiment 60 Synthesis of Labeled Intermediate 42r

Labeled Intermediate 42r is prepared by reactions with Intermediate 41s, wherein the ratio of raw materials, the solvents and the reaction conditions are the same as that of Embodiment 47, and the yield rate is 59.2%. $^1$H NMR (400 MHz, CDCl$_3$) δ8.00 (d, J=8.7 Hz, 2H), 7.95 (d, J=8.9 Hz, 1H), 7.37 (dd, J=5.5, 2.9 Hz, 3H), 7.10 (dd, J=8.9, 2.5 Hz, 1H), 4.24-4.09 (m, 3H), 3.88 (dd, J=11.4, 3.6 Hz, 1H), 3.79 (dd, J=11.3, 5.1 Hz, 1H), 3.32 (s, 3H), 1.48 (s, 9H), MS(ESI): m/z calcd for $C_{22}H_{26}N_2O_5S$ 430.16. found 431.21 (M+H)$^+$.

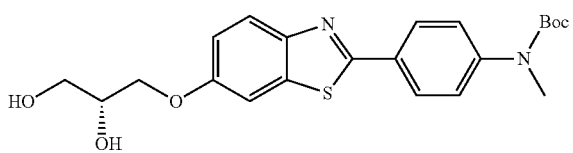 [SMILES: CN(C(=O)OC(C)(C)C)c1ccc(-c2nc3ccc(OC[C@H](O)CO)cc3s2)cc1]

Embodiment 61 Synthesis of Labeled Intermediate 43r

Intermediate 43r is prepared by reactions with Intermediate 42s, wherein the ratio of raw materials, the solvents and the reaction conditions are the same as that of Embodiment 49, and the yield rate is 14.0%. $^1$H NMR (400 MHz, CDCl$_3$) δ7.99 (d, J=8.6 Hz, 2H), 7.90 (d, J=8.9 Hz, 1H), 7.79 (d, J=8.2 Hz, 2H), 7.37 (d, J=8.5 Hz, 2H), 7.34-7.27 (m, 3H), 6.98 (dd, J=8.9, 2.4 Hz, 1H), 4.35-4.15 (m, 3H), 4.05 (s, 2H), 3.32 (s, 3H), 2.39 (s, 3H), 1.49 (s, 9H), MS(ESI): m/z calcd for $C_{29}H_{32}N_2O_7S_2$ 584.17. found 584.9 (M+H)$^+$.

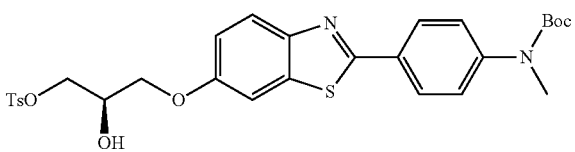 [SMILES: Cc1ccc(S(=O)(=O)OC[C@H](O)COc2ccc3nc(-c4ccc(N(C)C(=O)OC(C)(C)C)cc4)sc3c2)cc1]

Embodiment 62 Synthesis of Labeled Intermediate 43s

Intermediate 43s is prepared by reactions with Intermediate 42r, wherein the ratio of raw materials, the solvents and the reaction conditions are the same as that of Embodiment 49, and the yield rate is 14.4%. $^1$H NMR (400 MHz, CDCl$_3$) δ7.99 (d, J=8.7 Hz, 2H), 7.91 (d, J=8.9 Hz, 1H), 7.79 (d, J=8.3 Hz, 2H), 7.37 (d, J=8.6 Hz, 2H), 7.33-7.26 (m, 3H), 6.98 (dd, J=8.9, 2.5 Hz, 1H), 4.35-4.16 (m, 3H), 4.12-4.00 (m, 2H), 3.32 (s, 3H), 2.39 (s, 3H), 1.49 (s, 9H), MS(ESI): m/z calcd for $C_{29}H_{32}N_2O_7S_2$ 584.17. found 584.8 (M+H)$^+$.

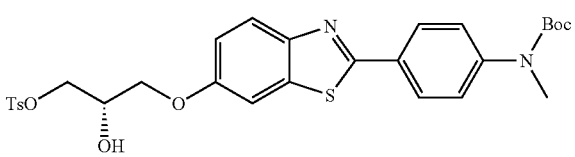 [SMILES: Cc1ccc(S(=O)(=O)OC[C@@H](O)COc2ccc3nc(-c4ccc(N(C)C(=O)OC(C)(C)C)cc4)sc3c2)cc1]

Embodiment 63 Synthesis of Labeled Precursor 44r

Labeled Precursor 44r is prepared by reactions with Intermediate 43r, wherein the ratio of raw materials, the solvents and the reaction conditions are the same as that of Embodiment 51, and the yield rate is 66.8%. $^1$H NMR (400 MHz, CDCl$_3$) δ8.00 (d, J=8.6 Hz, 2H), 7.90 (d, J=9.0 Hz, 1H), 7.77 (dd, J=8.2, 6.2 Hz, 2H), 7.38 (d, J=8.6 Hz, 2H), 7.30-7.26 (m, 2H), 7.25 (s, 1H), 7.03-6.93 (m, 1H), 4.77 (dt, J=6.9, 3.7 Hz, 1H), 4.44-4.15 (m, 3H), 4.15-3.96 (m, 2H), 3.96-3.63 (m, 1H), 3.60-3.44 (m, 1H), 3.32 (s, 3H), 2.37 (s, 3H), 1.89-1.62 (m, 3H), 1.49 (s, 9H), MS(ESI): m/z calcd for $C_{34}H_{40}N_2O_8S_2$ 668.22. found 669.29 (M+H)$^+$.

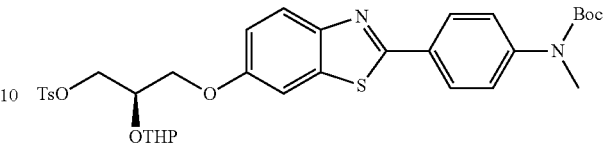

Embodiment 64 Synthesis of Labeled Precursor 44s

Labeled Precursor 44s is prepared by reactions with Intermediate 43s, wherein the ratio of raw materials, the solvents and the reaction conditions are the same as that of Embodiment 51, and the yield rate is 72.1%. $^1$H NMR (400 MHz, CDCl$_3$) δ8.00 (d, J=8.5 Hz, 2H), 7.91 (d, J=8.9 Hz, 1H), 7.77 (dd, J=8.1, 6.3 Hz, 2H), 7.37 (d, J=8.5 Hz, 2H), 7.32-7.26 (m, 2H), 7.26 (d, J=3.8 Hz, 2H), 6.96 (dt, J=8.9, 3.0 Hz, 1H), 4.88-4.69 (m, 1H), 4.40-4.14 (m, 3H), 4.14-3.92 (m, 2H), 3.90-3.68 (m, 1H), 3.59-3.43 (m, 1H), 3.32 (s, 3H), 2.38 (s, 3H), 1.87-1.63 (m, 3H), 1.48 (s, 9H), MS(ESI): m/z calcd for $C_{34}H_{40}N_2O_8S_2$ 668.22. found 669.1 (M+H)$^+$.

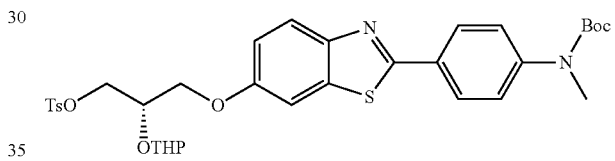

Embodiment 65 Synthesis of Labeled Intermediate 45r

Intermediate 45r is prepared by reactions with Compound 2, wherein the ratio of the raw material, the solvents and the reaction conditions are the same as that of Embodiment 41, and the yield rate is 54.1%. $^1$H NMR (400 MHz, d$_6$-DMSO) δ7.82 (t, J=9.3 Hz, 3H), 7.61 (s, 1H), 7.07 (d, J=8.9 Hz, 1H), 6.81 (d, J=8.8 Hz, 2H), 4.98 (d, J=5.2H z, 1H), 4.68 (s, 1H), 4.06 (s, 1H), 3.95 (s, 1H), 3.82 (s, 1H), 3.47 (s, 2H), 3.01 (s, 6H), MS(ESI): m/z calcd for $C_{18}H_{20}N_2O_3S$ 344.12. found 345.2 (M+H)$^+$.

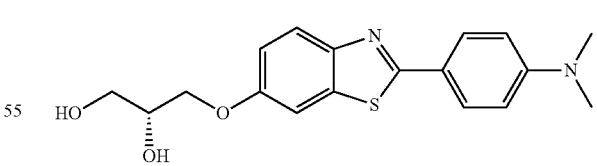

Embodiment 66 Synthesis of Labeled Intermediate 45s

Intermediate 45s is prepared by reactions with Compound 2, wherein the ratio of raw materials, the solvents and the reaction conditions are the same as that of Embodiment 41, and the yield rate is 89.2%. $^1$H NMR (400 MHz, d$_6$-DMSO) δ7.82 (s, 3H), 7.62 (s, 1H), 7.06 (d, J=9.0 Hz, 1H), 6.81 (d, J=6.1 Hz, 2H), 5.00 (s, 1H), 4.70 (s, 1H), 4.05 (s, 1H), 3.94 (s, 1H), 3.82 (s, 1H), 3.47 (s, 2H), 3.01 (s, 6H), MS(ESI): m/z calcd for $C_{18}H_{20}N_2O_3S$ 344.12. found 345.2 $(M+H)^+$.

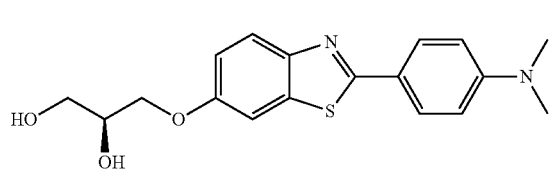 [SMILES: CN(C)c1ccc(-c2nc3ccc(OC[C@@H](O)CO)cc3s2)cc1]

Embodiment 67 Synthesis of Labeled Intermediate 46s

Intermediate 46s is prepared by reactions with Intermediate 45r, wherein the ratio of raw materials, the solvents and the reaction conditions are the same as that of Embodiment 49, and the yield rate is 8.8%. $^1$H NMR (400 MHz, CDCl$_3$) δ7.92 (d, J=8.5 Hz, 2H), 7.79 (d, J=8.3 Hz, 3H), 7.29 (d, J=8.1 Hz, 2H), 7.23 (d, J=2.4 Hz, 1H), 6.93 (dd, J=8.9, 2.4 Hz, 1H), 6.75 (d, J=8.8 Hz, 2H), 4.34-4.16 (m, 3H), 4.04 (d, J=4.2 Hz, 2H), 3.06 (s, 6H), 2.39 (s, 3H), MS(ESI): m/z calcd for $C_{25}H_{26}N_2O_5S_2$ 498.13. found 499.4 $(M+H)^+$.

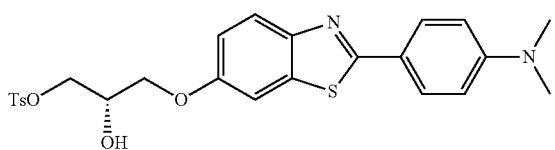 [SMILES: Cc1ccc(S(=O)(=O)OC[C@@H](O)COc2ccc3nc(-c4ccc(N(C)C)cc4)sc3c2)cc1]

Embodiment 68 Synthesis of Labeled Intermediate 46r

Intermediate 46r is prepared by reactions with Intermediate 45s, wherein the ratio of raw materials, the solvents and the reaction conditions are the same as that of Embodiment 49, and the yield rate is 7.0%. $^1$H NMR (400 MHz, CDCl$_3$) δ7.92 (d, J=8.2 Hz, 2H), 7.85 (d, J=8.8 Hz, 1H), 7.79 (d, J=7.9 Hz, 2H), 7.34-7.28 (m, 2H), 7.24 (s, 1H), 6.95 (dd, J=14.2, 9.1 Hz, 1H), 6.75 (d, J=8.5 Hz, 2H), 4.24 (s, 3H), 4.05 (s, 2H), 3.06 (s, 6H), 2.39 (s, 3H), MS(ESI): m/z calcd for $C_{25}H_{26}N_2O_5S_2$ 498.13. found 499.5 $(M+H)^+$.

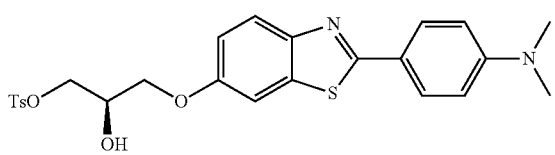 [SMILES: Cc1ccc(S(=O)(=O)OC[C@H](O)COc2ccc3nc(-c4ccc(N(C)C)cc4)sc3c2)cc1]

Embodiment 69 Synthesis of Labeled Precursor 47s

Labeled Precursor 47s is prepared by reactions with Intermediate 46s, wherein the ratio of raw materials, the solvents and the reaction conditions are the same as that of Embodiment 51, and the yield rate is 35.5%. $^1$H NMR (400 MHz, CDCl$_3$) δ7.91 (d, J=8.5 Hz, 2H), 7.83 (d, J=8.9 Hz, 1H), 7.77 (dd, J=8.1, 6.1 Hz, 2H), 7.29 (d, J=9.0 Hz, 1H), 7.25-7.17 (m, 2H), 6.90 (ddd, J=8.9, 4.3, 2.6 Hz, 1H), 6.75 (d, J=8.9 Hz, 2H), 4.86-4.70 (m, 1H), 4.43-4.11 (m, 4H), 4.13-3.96 (m, 2H), 3.95-3.66 (m, 2H), 3.65-3.40 (m, 2H), 3.05 (s, 6H), 2.37 (d, J=1.2 Hz, 3H), MS(ESI): m/z calcd for $C_{30}H_{34}N_2O_6S_2$ 582.19. found 582.9 $(M+H)^+$.

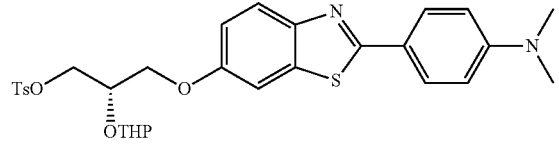

Embodiment 70 Synthesis of Labeled Precursor 47r

Labeled Precursor 47r is prepared by reactions with Intermediate 46r, wherein the ratio of raw materials, the solvents and the reaction conditions are the same as that of Embodiment 57, and the yield rate is 94.0%. $^1$H NMR (400 MHz, CDCl$_3$) δ7.92 (d, J=8.5 Hz, 2H), 7.83 (d, J=8.8 Hz, 1H), 7.80-7.70 (m, 2H), 7.35 (s, 1H), 7.25-7.14 (m, 2H), 6.90 (d, J=7.0 Hz, 1H), 6.75 (d, J=8.7 Hz, 2H), 4.42-3.96 (m, 5H), 3.97-3.68 (m, 3H), 3.64-3.35 (m, 2H), 3.05 (s, 6H), 2.37 (s, 3H), 1.89-1.38 (m, 4H), MS(ESI): m/z calcd for $C_{30}H_{34}N_2O_6S_2$ 582.19. found 583.5 $(M+H)^+$.

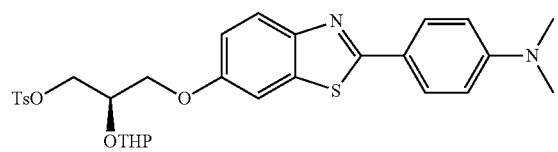

Embodiment 71 Synthesis of Labeled Intermediate 48r

Intermediate 48r is prepared by reactions with Compound 21, wherein the ratio of the raw material, the solvents and the reaction conditions are the same as that of Embodiment 41, and the yield rate is 56.0%. $^1$H NMR (400 MHz, d$_6$-DMSO) δ7.97 (d, J=9.0 Hz, 2H), 7.57 (d, J=8.8 Hz, 1H), 7.22 (d, J=2.4 Hz, 1H), 6.90 (dd, J=8.8, 2.5 Hz, 1H), 6.85 (d, J=9.1 Hz, 2H), 4.04 (dt, J=7.3, 3.7 Hz, 1H), 3.91 (dd, J=9.9, 6.1 Hz, 1H), 3.86-3.74 (m, 1H), 3.47 (d, J=5.7 Hz, 2H), 3.03 (s, 6H), MS(ESI): m/z calcd for $C_{18}H_{20}N_2O_4$ 328.14. found 329.17 $(M+H)^+$.

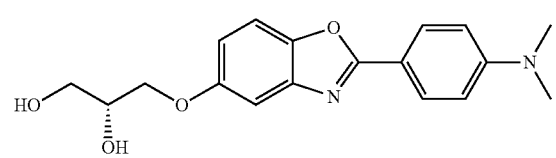 [SMILES: CN(C)c1ccc(-c2nc3cc(OC[C@H](O)CO)ccc3o2)cc1]

Embodiment 72 Synthesis of Labeled Intermediate 48s

Intermediate 48s is prepared by reactions with Compound 21, wherein the ratio of the raw material, the solvents and the reaction conditions are the same as that of Embodiment 41, and the yield rate is 52.2%. $^1$H NMR (400 MHz, d$_6$-DMSO) δ7.96 (d, J=5.7 Hz, 2H), 7.57 (d, J=8.4 Hz, 1H), 7.22 (s, 1H), 6.94-6.75 (m, 3H), 4.96 (s, 1H), 4.68 (s, 1H), 4.03 (s, 1H), 3.91 (s, 1H), 3.81 (s, 1H), 3.47 (s, 2H), 3.03 (s, 6H), MS(ESI): m/z calcd for $C_{18}H_{20}N_2O_4$ 328.14. found 329.3 $(M+H)^+$.

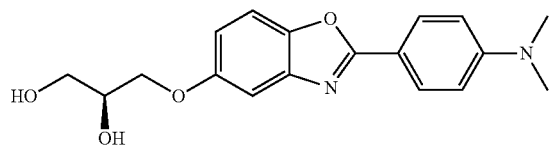 [SMILES: CN(C)c1ccc(-c2nc3cc(OC[C@@H](O)CO)ccc3o2)cc1]
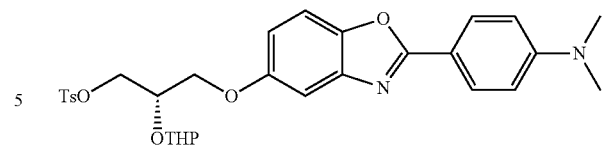

Embodiment 73 Synthesis of Labeled Intermediate 49s

Intermediate 49s is prepared by reactions with Compound 48r, wherein the ratio of raw materials, the solvents and the reaction conditions are the same as that of Embodiment 49, and the yield rate is 7.8%. $^1$H NMR (400 MHz, CDCl$_3$) δ8.07 (d, J=9.0 Hz, 2H), 7.78 (d, J=8.3 Hz, 2H), 7.36 (d, J=8.8 Hz, 1H), 7.29 (d, J=8.1 Hz, 2H), 7.10 (d, J=2.5 Hz, 1H), 6.80-6.70 (m, 3H), 4.35-4.18 (m, 3H), 4.01 (d, J=4.6 Hz, 2H), 3.06 (s, 6H), 2.39 (s, 3H), MS(ESI): m/z calcd for C$_{25}$H$_{26}$N$_2$O$_6$S 482.15. found 482.8 (M+H)$^+$.

Embodiment 76 Synthesis of Labeled Intermediate 50r

Labeled Precursor 50r is prepared by reactions with Compound 49r, wherein the ratio of raw materials, the solvents and the reaction conditions are the same as that of Embodiment 51, and the yield rate is 91.2%. $^1$H NMR (400 MHz, CDCl$_3$) δ8.09 (d, J=8.8 Hz, 2H), 7.78 (dd, J=8.2, 5.2 Hz, 2H), 7.36 (d, J=8.8 Hz, 1H), 7.30-7.26 (m, 1H), 7.27-7.20 (m, 2H), 7.09 (dd, J=7.6, 2.4 Hz, 1H), 6.78 (d, J=8.9 Hz, 2H), 4.88-4.70 (m, 1H), 4.44-4.14 (m, 4H), 3.96-3.75 (m, 5H), 3.61-3.44 (m, 4H), 3.08 (s, 6H), 2.38 (d, J=2.3 Hz, 3H), MS(ESI): m/z calcd for C$_{30}$H$_{34}$N$_2$O$_7$S 566.21. found 567.5 (M+H)$^+$.

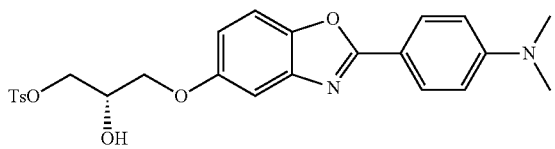 [SMILES: Cc1ccc(S(=O)(=O)OC[C@@H](O)COc2ccc3oc(-c4ccc(N(C)C)cc4)nc3c2)cc1]

Embodiment 74 Synthesis of Labeled Intermediate 49r

Intermediate 49r is prepared by reactions with Compound 48s, wherein the ratio of raw materials, the solvents and the reaction conditions are the same as that of Embodiment 49, and the yield rate is 25.8%. $^1$H NMR (400 MHz, CDCl$_3$) δ8.05 (d, J=9.0 Hz, 2H), 7.76 (d, J=8.3 Hz, 2H), 7.33 (d, J=8.8 Hz, 1H), 7.26 (s, 2H), 7.08 (d, J=2.4 Hz, 1H), 6.77-6.65 (m, 3H), 4.35-4.17 (m, 3H), 4.09-3.92 (m, 2H), 3.04 (s, 6H), 2.36 (s, 3H), MS(ESI): m/z calcd for C$_{25}$H$_{26}$N$_2$O$_6$S 482.15. found 483.4 (M+H)$^+$.

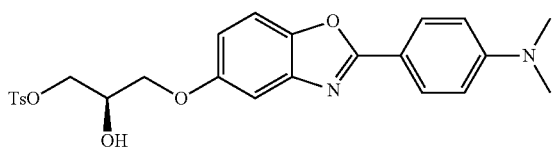 [SMILES: Cc1ccc(S(=O)(=O)OC[C@H](O)COc2ccc3oc(-c4ccc(N(C)C)cc4)nc3c2)cc1]

Embodiment 75 Synthesis of Labeled Precursor 50s

Labeled Precursor 50s is prepared by reactions with Compound 49s, wherein the ratio of raw materials, the solvents and the reaction conditions are the same as that of Embodiment 51, and the yield rate is 83.8%. $^1$H NMR (400 MHz, CDCl$_3$) δ8.07 (d, J=8.7 Hz, 2H), 7.80-7.75 (m, 2H), 7.35 (d, J=8.8 Hz, 1H), 7.27 (s, 1H), 7.26-7.24 (m, 1H), 7.07 (dd, J=8.4, 2.4 Hz, 1H), 6.76 (d, J=8.7 Hz, 2H), 4.90-4.70 (m, 1H), 4.40-4.10 (m, 3H), 4.10-3.90 (m, 2H), 3.90-3.70 (m, 1H), 3.60-3.40 (m, 1H), 3.07 (s, 6H), 2.37 (d, J=2.6 Hz, 3H), 1.60-1.40 (m, 6H), MS(ESI): m/z calcd for C$_{30}$H$_{34}$N$_2$O$_7$S 566.21. found 566.9 (M+H)$^+$.

Embodiment 77 Labeling of Compound [$^{18}$F]14r

Dissolve 2 mg of Labeled Precursor 44r to 1.7 mL of acetonitrile. Add the mixture to a reaction tube of dehydrated $^{18}$F$^-$ of a certain activity and containing K$_{222}$/K$_2$CO$_3$. Maintain the labeling at 100° C. for 12 min. After the mixture is cooled, add 0.20 mL of HCl (1M). After the swirling is completed, keep the reaction occurring for 5 min After the mixture is cooled, add a small amount of water and neutralize the mixture with NaHCO$_3$ until the mixture is alkaline. Separate the mixture with the C18 reverse phase column and rinse the mixture with water to remove salts and residual $^{18}$F$^-$. Then rinse the mixture with acetonitrile to obtain the final labeled product. After the mixture is dried with N$_2$, separate it with HPLC to obtain the labeled compound [$^{18}$F]14b with a purity of more than 98% and a labeling rate of approximately 5-40%, wherein the conditions of the HPLC separation are: water and C-18 semi-preparative column (10×250 mm, 5 μm); mobile phase: acetonitrile:water=3:2 (volume ratio); retention time: 9.09 min.

Embodiment 78 Labeling of Compound [$^{18}$F]14s

Compound [$^{18}$F]14s is prepared by reactions with Labeled Precursor 44s, wherein the ratio of raw materials, the solvents and the reaction conditions are the same as that of Embodiment 77, and the yield rate is approximately 5-40%. The conditions of the HPLC separation are: water and C-18 semi-preparative column (10×250 mm, 5 μm); mobile phase: acetonitrile:water=3:2 (volume ratio); retention time: 9.09 min.

Embodiment 79 Labelling of Compound [$^{18}$F]15r

Compound [$^{18}$F]15r is prepared by reactions with Labeled Precursor 47r, wherein the ratio of raw materials, the solvents and the reaction conditions are the same as that of Embodiment 77, and the yield rate is approximately 5-40%. The conditions of the HPLC separation are: water and C-18 semi-preparative column (10×250 mm, 5 μm); mobile phase: acetonitrile:water=3:2 (volume ratio); retention time: 15.23 min.

Embodiment 80 Labeling of Compound [$^{18}$F]15s

Compound [$^{18}$F]15s is prepared by reactions with Labeled Precursor 47s, wherein the ratio of raw materials, the solvents and the reaction conditions are the same as that of Embodiment 77, and the yield rate is approximately 5-40%. The conditions of the HPLC separation are: water and C-18 semi-preparative column (10×250 mm, 5 μm); mobile phase: acetonitrile:water=3:2 (volume ratio); retention time: 15.23 min.

Embodiment 81 Labeling of Compound [$^{18}$F]28r

Compound [$^{18}$F]28r is prepared by reactions with Labeled Precursor 38r, wherein the ratio of raw materials, the solvents and the reaction conditions are the same as that of Embodiment 77, and the yield rate is approximately 5-40%. The conditions of the HPLC separation are: water and C-18 semi-preparative column (10×250 mm, 5 μm); mobile phase: acetonitrile:water=3:2 (volume ratio); retention time: 7.95 min.

Embodiment 82 Labeling of Compound [$^{18}$F]28s

Compound [$^{18}$F]28s is prepared by reactions with Labeled Precursor 38s, wherein the ratio of raw materials, the solvents and the reaction conditions are the same as that of Embodiment 77, and the yield rate is approximately 5-40%. The conditions of the HPLC separation are: water and C-18 semi-preparative column (10×250 mm, 5 μm); mobile phase: acetonitrile:water=3:2 (volume ratio); retention time: 7.95 min.

Embodiment 83 Labeling of Compound [$^{18}$F]29r

Compound [$^{18}$F]29r is prepared by reactions with Labeled Precursor 50r, wherein the ratio of raw materials, the solvents and the reaction conditions are the same as that of Embodiment 77, and the yield rate is approximately 5-40%. The conditions of the HPLC separation are: water and C-18 semi-preparative column (10×250 mm, 5 μm); mobile phase: acetonitrile:water=3:2 (volume ratio); retention time: 12.58 min.

Embodiment 84 Labeling of Compound [$^{18}$F]29s

Compound [$^{18}$F]29s is prepared by reactions with Labeled Precursor 50s, wherein the ratio of raw materials, the solvents and the reaction conditions are the same as that of Embodiment 77, and the yield rate is approximately 5-40%. The conditions of the HPLC separation are: water and C-18 semi-preparative column (10×250 mm, 5 μm); mobile phase: acetonitrile:water=3:2 (volume ratio); retention time: 12.58 min.

Embodiment 85 An Experiment on the Effects of Labeled Precursors

The affinity of the compounds of the present invention is evaluated with the following competitive binding experiment and autoradiography experiment, which can be used as the enough evidence proving the compounds' high affinity to Aβ plaques. The absorption by the primitive brain and the removal from the brain of the labeled compounds are evaluated with an in-vivo biodistribution experiment on normal mice.

1. Competitive Binding Experiment

Competitive binding experiment ($K_i$ assay): Put a protein polymer $Aβ_{1-42}$ of a certain concentration and a radioactive ligand [$^{125}$I] IMPY of a certain concentration together so that a binding reaction can occur. Add the compounds to be tested and of different concentrations to this reaction system (Put the target compounds used in the embodiments of the present invention and [$^{125}$I] IMPY together respectively so that a competitive binding reaction can occur respectively. After the balance, separate the compounds, measure the radioactivity, and then calculate the inhibition constant ($K_i$).

1.1 Experiment Processes:

(1) Prepare 4 L of a PBS (0.2M) buffer solution with pH=7.4.

(2) Prepare a radioactive ligand [$^{125}$I] IMPY by an established method. The [$^{125}$I] IMPY is prepared as an aqueous solution of 100000 cpm/100 μL.

(3) The compounds to be tested are prepared as a series of ethanol solutions of $10^{-3}$ to $10^{-9}$ mol/L.

(4) A receptor $Aβ_{1-42}$ protein is prepared by an established method, being diluted into an aqueous solution of approximately 30 nM.

(5) A glass fiber filter is soaked in a PBS solution containing 0.1% (volume fraction) of polyethyleneimine for 0.5 h.

(6) Add 100 μL of a solution of a compound to be tested and of different concentrations, 100 μL of the [$^{125}$I] IMPY solution, 700 μL of the PBS solution and 100 μL of the $Aβ_{1-42}$ solution to a 12×75 mm borosilicate glass tube. Seal the tub with parafilm and swirl it.

(7) Shake the tube in a water bath constantly at 37° C. and maintain the incubation for 2 h.

(8) Collect the reaction solution with a multi-phase cell collector. Rinse the collected solution with the PBS for three times, 3 mL for each rinse.

(9) Count with a γ counter.

(10) Process the data.

1.2 Results of the Experiments:

The half inhibition constant ($IC_{50}$) obtained from the competitive binding experiments and the inhibition constants calculated with formulas are shown in Table 1.

TABLE 1

The Inhibition Constants of Labeled Compounds

| Compound | Substituent R2 | Configuration | R | X | Y | Z | $K_i$ (nM) |
|---|---|---|---|---|---|---|---|
| 14s | 6 | S | NHCH$_3$ | N | S | CH | 26.0 ± 6.5 |
| 14r | 6 | R | NHCH$_3$ | N | S | CH | 27.2 ± 2.9 |
| 15s | 6 | S | N(CH$_3$)$_2$ | N | S | CH | 3.7 ± 1.1 |
| 15r | 6 | R | N(CH$_3$)$_2$ | N | S | CH | 3.2 ± 1.1 |
| 16s | 6 | S | NHCH$_3$ | N | S | N | 45.4 ± 11.8 |
| 16r | 6 | R | NHCH$_3$ | N | S | N | 9.9 ± 2.8 |
| 17s | 6 | S | N(CH$_3$)$_2$ | N | S | N | 27.2 ± 7.1 |
| 17r | 6 | R | N(CH$_3$)$_2$ | N | S | N | 11.1 ± 5.4 |
| 18s | 6 | S | NHCH$_3$ | N | O | CH | 103.2 ± 18.6 |
| 18r | 6 | R | NHCH$_3$ | N | O | CH | 128.6 ± 40.2 |
| 19s | 6 | S | N(CH$_3$)$_2$ | N | O | CH | 11.0 ± 1.5 |
| 19r | 6 | R | N(CH$_3$)$_2$ | N | O | CH | 10.8 ± 2.6 |
| 28s | 5 | S | NHCH$_3$ | N | O | CH | 67.3 ± 5.5 |
| 28r | 5 | R | NHCH$_3$ | N | O | CH | 85.3 ± 5.2 |
| 29s | 5 | S | N(CH$_3$)$_2$ | N | O | CH | 15.5 ± 3.2 |

TABLE 1-continued

The Inhibition Constants of Labeled Compounds

| Compound | Substituent R2 | Configuration | R | X | Y | Z | $K_i$ (nM) |
|---|---|---|---|---|---|---|---|
| 29r | 5 | R | N(CH$_3$)$_2$ | N | O | CH | 7.6 ± 2.8 |
| 30s | 5 | S | NHCH$_3$ | N | O | N | 195.6 ± 49.1 |
| 30r | 5 | R | NHCH$_3$ | N | O | N | 186.8 ± 39.0 |
| 31s | 5 | S | N(CH$_3$)$_2$ | N | O | N | 57.4 ± 7.6 |
| 31r | 5 | R | N(CH$_3$)$_2$ | N | O | N | 27.2 ± 6.3 |
| IMPY | — | — | — | — | — | — | 10.5 ± 1.0 |

2. The In-Vivo Biodistribution Experiment on Normal Mice

The in-vivo pharmacokinetic properties of mice have been studied with the in-vivo biodistribution experiment, especially the absorption by the primitive brain and the removal from the brain.

2.1 Experiment Processes:

Inject 5-10 μCi of a labeled compound (100 μL of a physiological saline solution containing 5% of ethanol) into normal mice (ICR, male, 20-22 g) (n=5) by tail vein injection. The mice are decapitated respectively 2 minutes, 10 minutes, 30 minutes and 60 minutes after the injection. Dissect the mice and take out the relevant organs. Measure the moisture content and the radioactivity amount. The measurement values represent the percentage of the radioactivity amount in an organ (% ID/organ) and the percentage of the radioactivity amount in the organ of one gram (% ID/g).

2.2 Results of the Experiments

The results of the experiments are shown in Table 2. The $^{18}$F labeled compound of the present invention can smoothly get through the brain blood barrier, with the primitive brain's high absorption in two minutes, and especially, the primitive brain can absorb Compound [$^{18}$F]29s more quickly which can be as well quickly removed from the brain of normal mice, wherein the ratio of the absorption in 2 minutes to that in 60 minutes is 27.8.

TABLE 2

The In-Vivo Biodistribution Experiment of $^{18}$F Labeled Compounds (% ID/g) Administered to Normal Mice

| Organs | 2 min. | 10 min | 30 min | 1 h |
|---|---|---|---|---|
| [$^{18}$F]15r | | | | |
| Blood Brain | 2.90 ± 0.16 | 2.19 ± 0.19 | 1.63 ± 0.11 | 1.39 ± 0.11 |
| Bones | 13.41 ± 2.00 | 13.00 ± 0.76 | 8.73 ± 1.05 | 3.43 ± 0.58 |
|  | 2.43 ± 0.53 | 2.31 ± 0.26 | 1.42 ± 0.27 | 1.12 ± 0.59 |
| [$^{18}$F]15s | | | | |
| Blood Brain | 3.28 ± 0.36 | 2.20 ± 0.09 | 1.93 ± 0.66 | 0.95 ± 0.04 |
| Bones | 8.95 ± 0.61 | 10.55 ± 0.41 | 5.65 ± 1.21 | 1.69 ± 0.31 |
|  | 2.31 ± 0.71 | 1.82 ± 0.39 | 1.45 ± 0.48 | 1.08 ± 0.38 |
| [$^{18}$F]28s | | | | |
| Blood Brain | 3.44 ± 0.16 | 1.59 ± 0.10 | 0.71 ± 0.04 | 0.40 ± 0.07 |
| Bones | 6.67 ± 0.34 | 2.18 ± 0.28 | 0.50 ± 0.04 | 0.29 ± 0.06 |
|  | 1.63 ± 0.44 | 0.77 ± 0.11 | 0.52 ± 0.16 | 0.74 ± 0.13 |
| [$^{18}$F]28r | | | | |
| Blood Brain | 3.70 ± 0.42 | 2.24 ± 0.15 | 1.74 ± 0.11 | 1.62 ± 0.16 |
| Bones | 9.27 ± 1.19 | 3.47 ± 0.32 | 1.48 ± 0.61 | 1.27 ± 0.15 |
|  | 1.41 ± 0.29 | 1.79 ± 0.21 | 1.19 ± 0.15 | 3.05 ± 0.86 |
| [$^{18}$F]29r | | | | |
| Blood Brain | 2.97 ± 0.30 | 2.19 ± 0.25 | 2.05 ± 0.08 | 1.88 ± 0.13 |
| Bones | 9.16 ± 0.34 | 6.27 ± 0.37 | 2.23 ± 0.26 | 1.58 ± 0.10 |
|  | 2.12 ± 0.60 | 1.24 ± 0.40 | 1.36 ± 0.41 | 1.93 ± 0.77 |
| [$^{18}$F]29s | | | | |
| Blood Brain | 3.34 ± 0.25 | 1.58 ± 0.10 | 0.85 ± 0.11 | 0.52 ± 0.07 |
| Bones | 9.46 ± 0.58 | 5.00 ± 0.28 | 0.94 ± 0.13 | 0.34 ± 0.03 |
|  | 2.06 ± 0.45 | 0.99 ± 0.35 | 0.85 ± 0.30 | 1.13 ± 0.28 |

Albeit the detailed general description and specific embodiments of the present invention have been given hereinabove, further modifications and improvements can be made on the basis of the present invention, and this is the common knowledge of the skilled technical staff in this field. Therefore, the modifications and improvements not deviating from the present invention shall be within the scope of the claims of the present invention.

What is claimed is:

1. A preparation method of a compound shown as Formula (I):

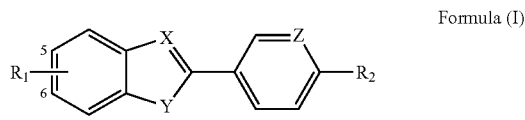

Formula (I)

wherein X is N; Y is S; Z is N; R$_1$ is

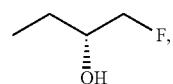

F in R$_1$ is $^{18}$F; and R$_2$ is N(CH$_3$)$_2$, wherein the preparation method of the compound consists of steps of:

(1) dissolving 1 mmol of

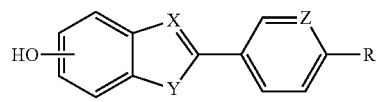

in 30 mL of anhydrous ethanol and adding 0.3 mL of a 200 g/L NaOH solution to a mixture thereof, wherein X is N; Y is S; Z is N; R is N(CH$_3$)$_2$; stirring the mixture in an oil bath at 80° C. until reflux lasts for 1 h; adding 1.5 mmol of

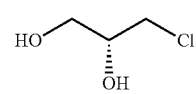

to the mixture; after reaction is completed, removing a solvent; wherein after column chromatography separation, a compound with a Formula (VI) shown below is obtained:

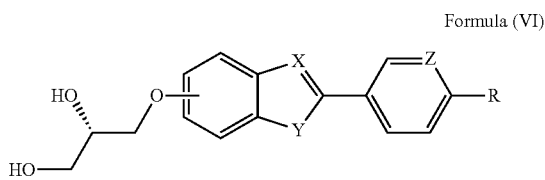

Formula (VI)

(2) when R is NHCH₃, dissolving 1 mmol of the compound with the Formula (VI), 8 mmol of imidazole and 8 mmol of tert-butyldimethylsilyl chloride in 30 mL of a CH₂Cl₂ solution; stirring a mixture thereof in an oil bath at 40° C. until reflux lasts for 5 h; after reaction is completed, removing CH₂Cl₂; wherein after the column chromatography separation, a compound with a Formula (VIII) shown below is obtained:

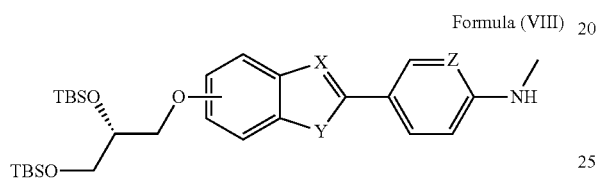

Formula (VIII)

(3) dissolving 1 mmol of the compound with the Formula (VIII) in 30 mL of a THF solution and adding an excessive dose of (Boc)₂O (Di-tert-butyl decarbonate) to a mixture thereof; stirring the mixture in an oil bath at 80° C. until reflux lasts for a night; after reaction is completed, removing the THF; wherein after the column chromatography separation, a compound with a Formula (XI) shown below is obtained:

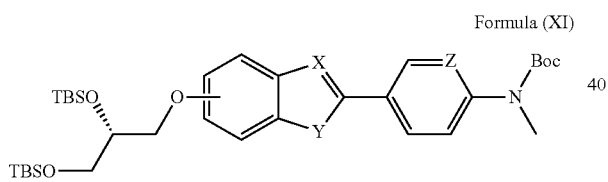

Formula (XI)

(4) dissolving 1 mmol of the compound with the Formula (XI) in 30 mL of the THF solution and adding 7 mmol of TBAF to a mixture thereof; stirring the mixture in an oil bath at 30° C. until reflux lasts for one night; after reaction is completed, removing the THF; wherein after the column chromatography separation, a compound with a Formula (XII) shown below is obtained:

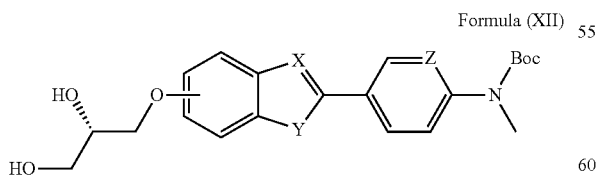

Formula (XII)

(5) dissolving 1 mmol of the compound with the Formula (VI) and 1 mmol of the compound with the Formula (XII) in 5 mL of pyridine respectively and adding 1.5 mmol of TsCl to a mixture thereof; stirring the mixture in an ice bath at 0° C. until reactions occur; after the reactions are completed, removing the pyridine; wherein after the column chromatography separation, a compound with a Formula (XV) shown below is obtained:

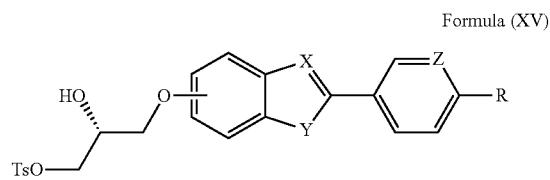

Formula (XV)

wherein X is N; Y is S; Z is N; R is N(CH₃)₂;

(6) dissolving 1 mmol of the compound with the Formula (XV), 4 mmol of 3,4-dihydro-2H-pyran and 0.2 mmol of PPTS (Pyridinium p-toluenesulfonate) in 30 mL of a CH₂Cl₂ solution respectively; stirring a mixture thereof in an oil bath at 40° C. until reflux lasts for a night; after reaction is completed, removing CH₂Cl₂; wherein after the column chromatography separation, a compound with a Formula (XVII) shown below is obtained:

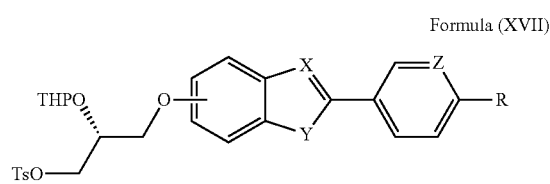

Formula (XVII)

and (7) dissolving 10 mg of the compound with the Formula (XVII) in 2 mL of acetonitrile; adding a mixture thereof to a reaction tube of dehydrated $^{18}F^-$ and $K_{222}/K_2CO_3$; maintaining labeling at 100° C. for 12 min; after the mixture is cooled, adding 0.15 mL of 1M HCl; after swirling is completed, keeping reacting for 5 min; after the mixture is cooled, adding a small amount of water and neutralizing the mixture with NaHCO₃ until the mixture is alkaline; separating the mixture with a C18 reverse phase column and rinsing the mixture with water to remove salts and residual $^{18}F^-$; then rinsing the mixture with the acetonitrile; after the mixture is dried with N₂, separating with HPLC to obtain a compound with a Formula (XIV) shown below:

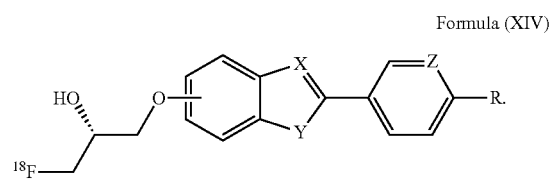

Formula (XIV)

* * * * *